(12) United States Patent
Hao et al.

(10) Patent No.: US 7,241,758 B2
(45) Date of Patent: Jul. 10, 2007

(54) COMPOUNDS USEFUL AS ANTI-INFLAMMATORY AGENTS

(75) Inventors: Ming-Hong Hao, Ridgefield, CT (US); Sanxing Sun, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 489 days.

(21) Appl. No.: 10/271,301

(22) Filed: Oct. 15, 2002

(65) Prior Publication Data

US 2003/0125354 A1 Jul. 3, 2003

Related U.S. Application Data

(62) Division of application No. 09/714,539, filed on Nov. 16, 2000, now Pat. No. 6,492,393.

(51) Int. Cl.
  C07D 401/12 (2006.01)
  C07D 401/14 (2006.01)
  A61K 31/4427 (2006.01)
  A61P 19/02 (2006.01)

(52) U.S. Cl. .............. 514/227.8; 514/231.5; 514/252.03; 514/253.01; 514/255.05; 514/256; 514/300; 514/336; 514/337; 514/332; 514/357; 546/118; 546/122; 546/256; 546/272.7; 546/119; 546/255; 546/273.4; 546/272.4; 546/275.4; 544/60; 544/238; 544/124; 544/333; 544/357; 544/360

(58) Field of Classification Search .............. 514/307, 514/313, 340, 353, 227.8, 231.5, 252.03, 514/253.01, 255.05, 256, 300, 332, 337, 514/336, 357; 546/143, 159, 281.4, 306, 546/118, 119, 122, 255, 256, 272.7, 273.4, 546/272.4, 275.4; 544/60, 124, 238, 333, 544/357, 360
See application file for complete search history.

(56) References Cited

U.S. PATENT DOCUMENTS

| | | | |
|---|---|---|---|
| 4,435,567 A | 3/1984 | Lugosi et al. | |
| 4,997,844 A | 3/1991 | Bernstein et al. | |
| 5,162,360 A | 11/1992 | Creswell | |
| 5,596,001 A | 1/1997 | Hamanaka | |
| 6,166,028 A * | 12/2000 | Bloom et al. ............. | 514/277 |
| 6,319,939 B1 * | 11/2001 | Mabire et al. ............. | 514/381 |

FOREIGN PATENT DOCUMENTS

| | | |
|---|---|---|
| EP | 0 418 071 | 3/1991 |
| EP | 0 395 144 | 10/1994 |
| WO | WO 93/24458 | 12/1993 |
| WO | WO 94/18170 | 8/1994 |
| WO | WO 96/25157 | 8/1996 |
| WO | WO 96/39382 A1 | 12/1996 |
| WO | WO 97/16442 | 5/1997 |
| WO | WO 98/5255 | 11/1998 |
| WO | WO 99/21835 A1 | 5/1999 |
| WO | WO 99/23091 | 5/1999 |
| WO | WO 99/32106 | 7/1999 |
| WO | WO 99/32110 | 7/1999 |
| WO | WO 99/32111 | 7/1999 |
| WO | WO 99/32463 | 7/1999 |
| WO | WO 00/55139 | 9/2000 |
| WO | WO 00/55152 | 9/2000 |
| WO | US/00/31582 | 11/2000 |
| WO | WO 01/07403 A1 | 2/2001 |

OTHER PUBLICATIONS

Manuela G. Neuman, "Cytokines-central factors in alcoholic liver disease," Winter 2003, Alcohol Research and Health, pp. 1-13.*
Chalmers (TiPS vol. 17, pp. 166-172 Apr. 1996).*
Mukhopadhyay et al. Respiratory Research 2006, 7:125 pp. 1-9.*
http://www.permanente.net/homepage/kaiser/pages/f46315.html, downloaded on Nov. 13, 2006.*
Lipton, James, M., Peptide Modulation of Inflammatory Processes within the Brain, Neuroimmunomodulation 1998: 5:178-183.
Li, Dayuan, Kinetics of tumor necrosis factor a in plasma and the cardioprotective effect of a monoclonal antibody to tumor necrosis factor a in acute myocardial infarction.; American Heart Journal, Jun. 1999; 1146-1152.
Raine, C.S., Multiple sclerosis: expression of molecules of the tumor necrosis factor ligand and receptor families in relationship to the demyelinated plaque. Rev Neurol (Paris) 1998; 8-9, 577-585.
Renzetti, L.M., Ro 45-2081, a TNF receptor fusion protein, prevents inflammatory responses in the airways.,Inflamm Res. 46, Supplement 2, {1997} S143-S144.
Viscardi, R.M., Inflammatory cytokine mRNAs in surgical specimens of necrotizing enterocolitis and normal newborn intestine., Pediatric Pathology & Laboratory Medicine, 17: 547-559, 1997.

* cited by examiner

*Primary Examiner*—Kahsay Habte
(74) *Attorney, Agent, or Firm*—Michael Morris; Mary-Ellen M. Devlin; Anthony P. Bottino

(57) ABSTRACT

Disclosed are novel aromatic compounds of the formula (I) wherein G, X, Ar, L and Q are defined herein. The compounds are useful in pharmaceutic compositions for treating diseases or pathological conditions involving inflammation such as chronic inflammatory diseases. Also disclosed are processes of making such compounds

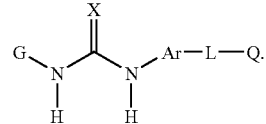

(I)

12 Claims, No Drawings

COMPOUNDS USEFUL AS ANTI-INFLAMMATORY AGENTS

RELATED APPLICATION DATA

This application is a divisional application of U.S. Pat. No. 6,492,393 filed Nov. 16, 2000.

TECHNICAL FIELD OF THE INVENTION

This invention relates to novel compounds of formula(I):

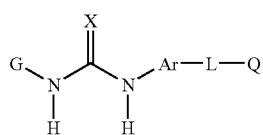

(I)

wherein G, X, Ar, L and Q of formula(I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050). GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferonγ (IFNγ) has been implicated in a number of diseases. It has been associated with increased collagen deposition that is a central histopathological feature of graft-versus-host disease (Parkman, 1998, *Curr Opin Hema-* tol. 5, 22). Following kidney transplantation, a patient was diagnosed with acute myelogenous leukemia. Retrospective analysis of peripheral blood cytokines revealed elevated levels of GM-CSF and IFNγ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFNγ (Ablumunits, et al., 1998, *J Autoimmun.* 11, 73). IFNγ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFNγ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFNγ following challenge with Vespula venom (Bonay, et al., 1997, *Clin Exp Immunol.* 109, 342). The expression of a number of cytokines, including IFNγ has been shown to increase following a delayed type hypersensitivity reaction thus indicating a role for IFNγ in atopic dermatitis (Szepietowski, et al., 1997, *Br J Dermatol.* 137, 195). Histopathologic and immunohistologic studies were performed in cases of fatal cerebral malaria. Evidence for elevated IFNγ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFNγ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFNγ, TNF and IL-2 (Chisari, et al., 1995, *Springer Semin Immunopathol.* 17, 261). IFNγ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al, 1996, *J Bone Miner Res.* 11, 300). Studies with gene deficient mice have demonstrated that the IL-12 dependent production of IFNγ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFNγ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFNγ was negatively correlated with serum IgE suggesting a role for IFNγ in atopic patients (Teramoto et al., 1998, *Clin Exp Allergy* 28, 74).

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In one embodiment of the invention there are provided compounds of the formula (I):

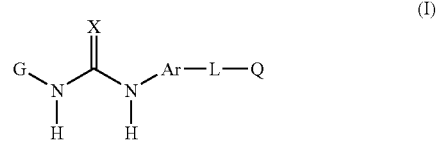

wherein:

G is:

an aromatic $C_{6-10}$ carbocycle or a nonaromatic $C_{3-10}$ carbocycle saturated or unsaturated;

a 6-10 membered heteroaryl containing 1 or more heteroatoms chosen from O, N and S; or a 5-8 membered monocyclic heterocycle or a 8-11 membered bicyclic heterocycle, each containing one or more heteroatoms chosen from O, N and S;

wherein G is substituted by one or more $R_1$, $R_2$ or $R_3$;

Ar is:
phenyl, naphthyl, quinolinyl, isoquinolinyl, tetrahydronaphthyl, tetrahydroquinolinyl, dihydrobenzofuranyl, dihydrobenzothienyl, indolenyl, benzothiophenyl, tetrahydroisoquinolinyl, benzimidazolyl, benzofuranyl, indanyl, indenyl or indolyl each optionally substituted by one or more $R_4$ or $R_5$ groups;

L is a:
$C_{1-10}$ saturated or unsaturated branched or unbranched carbon chain;
wherein one or more methylene groups are optionally independently replaced by heteroatoms chosen from O, N and $S(O)_m$; and
wherein said L is optionally substituted with 0-2 oxo groups and one or more $C_{1-4}$ branched or unbranched alkyl optinally substituted by one or more halogen atoms;

Q is:
phenyl, naphthyl, pyridinyl, pyrimidinyl, pyridazinyl, imidazolyl, benzimidazolyl, furanyl, thienyl, pyranyl, naphthyridinyl, pyrazinyl, pyrazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl, which are optionally substituted with one to three $C_{1-6}$ alkyl, $C_{1-6}$ alkoxy, hydroxy, amino, mono- or di-($C_{1-3}$ alkyl)amino, mono- or di-(phenyl-$C_{1-3}$ alkyl)amino, $C_{1-6}$ alkyl-$S(O)_m$, phenyl-$C_{1-3}$-alkoxy or phenylamino wherein the phenyl ring is optionally substituted with one to two halogen, $C_{1-6}$ alkyl or $C_{1-6}$ alkoxy;
tetrahydropyranyl, tetrahydrofuranyl, 1,3-dioxolanone, 1,3-dioxanone, 1,4-dioxanyl, morpholino, thiomorpholino, thiomorpholino sulfoxide, thiomorpholino sulfone, piperazinyl, piperidinyl, piperidinonyl, tetrahydropyrimidonyl, cyclohexanone, cyclohexanol, pentamethylene sulfide, pentamethylene sulfoxide, pentamethylene sulfone, tetramethylene sulfide, tetramethylene sulfoxide or tetramethylene sulfone which are optionally substituted with one to three $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl or $C_{1-3}$ alkoxy-$C_{1-3}$ alkyl;
$C_{1-6}$ alkoxy, secondary or tertiary amine wherein the amino nitrogen is covalently bonded to $C_{1-3}$ alkyl or $C_{1-5}$ alkoxyalkyl, phenylamino, wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$ or phenyl-$S(O)_m$ wherein the phenyl ring is optionally substituted with one to two halogen, $C_{1-6}$ alkoxy, hydroxy or mono- or di-($C_{1-3}$ alkyl)amino;

each $R_1$ is independently:
$C_{3-10}$ branched or unbranched alkyl optionally partially or fully halogenated, and optionally substituted with one to three $C_{3-10}$ cycloalkyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C(O)$ or mono- or di($C_{1-3}$)alkylaminocarbonyl;
cyclopropyl, cyclobutyl, cyclopentanyl, cyclohexanyl, cycloheptanyl, bicyclopentanyl, bicyclohexanyl or bicycloheptanyl, which are optionally partially or fully halogenated and optionally substituted with one to three $C_{1-3}$ alkyl groups optionally partially or fully halogenated, cyano, hydroxy $C_{1-3}$alkyl or aryl; or an analog of cyclopropyl, cyclobutyl, cyclopentanyl, cyclohexanyl, cycloheptanyl, bicyclopentanyl, bicyclohexanyl or bicycloheptanyl wherein one to three ring methylene groups are replaced independently by O, $S(O)_m$, CHOH, >C=O, >C=S or NH;
$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned are optionally substituted with 1 to 5 halogen, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclohexanyl or bicycloheptanyl, hydroxy, cyano, $C_{1-3}$ alkoxy optionally partially or fully halogenated, $NH_2C(O)$ or mono- or di($C_{1-3}$)alkylaminocarbonyl; the $C_{3-10}$ branched or unbranched alkenyl is optionally interrupted by one or more O, N or $S(O)_m$;
cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;
cyano, halogen;
methoxycarbonyl, ethoxycarbonyl or propoxycarbonyl;
silyl containing three $C_{1-4}$ independently branched or unbranched alkyl groups optionally partially or fully halogenated;
$C_{2-6}$ branched or unbranched alkyl-C(O), $C_{2-6}$ branched or unbranched-S, $C_{2-6}$ branched or unbranched-S(O), $C_{2-6}$ branched or unbranched-$S(O)_2$;
$C_{2-6}$ alkynyl branched or unbranched carbon chain optionally partially or fully halogenated, wherein one or more methylene groups are optionally replaced by O, NH and $S(O)_m$ and wherein said alkynyl group is optionally independently substituted with 0-2 oxo groups, pyrroldinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms;

each $R_2$, $R_4$, and $R_5$ is independently
a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;
$C_{1-6}$ alkoxy, hydroxy, amino, or mono- or di-($C_{1-4}$ alkyl)amino, cyano, halogen;
OR-$_6$;
nitro; or
mono- or di-($C_{1-4}$ alkyl)amino-$S(O)_2$ optionally partially or fully halogenated, or $H_2NSO_2$;

each $R_3$ is independently:
hydrogen, phenyl, naphthyl, pyridinyl, pyrimidinyl, pyrazinyl, pyridazinyl, pyrrolyl, pyrrolidinyl, imidazolyl, pyrazolyl, thienyl, furyl, tetrahydrofuryl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl wherein each of the aforementioned is optionally substituted with one to five phenyl, naphthyl, heterocycle or heteroaryl wherein the heterocyclic and hetearyl moiety is as hereinabove described in this paragraph, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, cyano, $C_{1-3}$ alkoxy optionally partially or fully halogenated, phenyloxy, naphthyloxy, heteraryloxy wherein the heterocyclic moiety is as hereinabove described in this paragraph, nitro, amino, mono- or di-($C_{1-3}$)alkylamino, phenylamino, naphthylamino, heterocyclic or heteroaryl amino wherein the heterocyclic or heteroaryl moiety is as hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy-mono- or di-($C_{1-5}$)-alkyl-amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclic ring is optionally independently substituted with 1 to 3 groups selected from phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ branched or unbranched alkyl optionally partially or fully halogenated, halo, cyano, $C_{1-3}$ alkoxy optionally partially or fully halogenated, phenyloxy, naphthyloxy, heterocyclicoxy heteroaryloxy wherein the heterocyclic or heteroaryl moiety is as hereinabove described in this paragraph, nitro, amino, mono- or di-($C_{1-3}$)alkylamino, phenylamino, naphthylamino, heterocyclicamino or heteroarylamino wherein the heterocyclic or heteroaryl moiety is as hereinabove described in this paragraph, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl and $R_{15}$—$C_{1-5}$ alkyl($R_{16}$)N;

cyclopropyl, cyclobutyl, cyclopentanyl, cyclohexanyl, cycloheptanyl, bicyclopentanyl, bicyclohexanyl or bicycloheptanyl optionally partially or fully halogenated and optionally substituted with one to three $C_{1-3}$ alkyl groups, or an analog of cyclopropyl, cyclobutyl, cyclopentanyl, cyclohexanyl, cycloheptanyl, bicyclopentanyl, bicyclohexanyl or bicycloheptanyl wherein one to three ring methylene groups are replaced independently by O, $S(O)_m$, CHOH, >C=O, >C=S or NH;

cyclopentenyl, cyclohexenyl, cyclohexadienyl, cycloheptenyl, cycloheptadienyl, bicyclohexenyl or bicycloheptenyl each optionally substituted with one to three $C_{1-3}$ alkyl groups;

$C_{1-4}$ branched or unbranched alkyl-phenyl-C(O)—$C_{0-4}$ branched or unbranched alkyl, $C_{1-4}$ branched or unbranched alkyl-C(O)—$C_{0-4}$ branched or unbranched alkyl, $C_{1-4}$ branched or unbranched alkyl-phenyl-$S(O)_m$—$C_{0-4}$ branched or unbranched alkyl;

$C_{1-6}$ branched or unbranched alkyl or $C_{1-6}$ branched or unbranched alkoxy each is optionally partially or fully halogenated or optionally substituted with $R_{17}$;

$C_{0-6}$ branched or unbranched alkyl optionally substituted with $OR_{18}$;

amino or $C_1$-$C_5$ branched or unbranched mono- or di-alkylamino optionally substituted with $R_{19}$;

Cyclopropyloxy, cyclobutyloxy, cyclopentyloxy, cyclohexyloxy or cycloheptyloxy which are optionally partially or fully halogenated and optionally substituted with one to three $C_{1-3}$ alkyl groups optionally partially or fully halogenated, wherein one to three ring methylene groups are replaced independently by O, $S(O)_m$, CHOH, >C=O, >C=S or NH;

$R_{20}C(O)N(R_{21})$—, $R_{22}O$— or $R_{23}R_{24}NC(O)$—; $R_{26}(CH_2)_mC(O)N(R_{21})$— or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain optionally partially or fully halogenated, wherein one or more methylene groups are optionally replaced by O, NH, S(O), $S(O)_2$ or S and wherein said alkynyl group is optionally independently substituted with 0-2 oxo groups, pyrroldinyl, pyrrolyl, one or more $C_{1-4}$ branched or unbranched alkyl optionally substituted by one or more halogen atoms, nitrile, morpholino, piperidine, piperazine, imidazole, phenyl, pyridine, tetrazole, or $C_{1-4}$ branched or unbranched alkylamino optioanlly substituted by one or more halogen atoms; or aroyl;

$R_6$ is a:

$C_{1-4}$ branched or unbranched alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently:

nitrile, morpholino, piperidinyl, piperazinyl, imidazolyl, phenyl, pyridinyl, tetrazolyl or alkylamino mono- or di-$C_{0-4}$ branched or unbranched optionally partially or fully halogenated;

each $R_{11}$ and $R_{16}$ is independently:

hydrogen or $C_{1-4}$ branched or unbranched alkyl optionally partially or fully halogenated;

$R_{18}$ is independently:

hydrogen or a $C_{1-4}$ branched or unbranched alkyl optionally independently substituted with oxo or $R_{25}$;

$R_{20}$ is:

$C_{1-10}$ branched or unbranched alkyl optionally partially or fully halogenated, phenyl or pyridinyl;

$R_{21}$ is:

hydrogen or $C_{1-3}$ branched or unbranched alkyl optionally partially or fully halogenated;

each $R_{22}$, $R_{23}$ and $R_{24}$ is independently:

hydrogen, $C_{1-6}$ branched or unbranched alkyl optionally substituted by carbonylamino- mono- or di-$C_{1-3}$alkyl or amino-mono- or di$C_{1-3}$alkyl or wherein said $C_{1-6}$ alkyl optionally partially or fully halogenated and optionally interrupted by one or more O, N or S, phenyl, pyridine, mono- or di-$C_{0-4}$ branched or unbranched alkyl optionally partially or fully halogenated and alkylamino;

or $R_{23}$ and $R_{24}$ taken together optionally form a heterocyclic or heteroaryl ring;

m=0, 1 or 2;

X=O or S; and the pharmaceutically acceptable derivatives thereof.

In another embodiment of the invention there is provided compounds of the formula(I) as described immmediately above, and wherein G is phenyl, naphthyl, benzocyclobutanyl, dihydronaphthyl, tetrahydronaphthyl, benzocycloheptanyl, benzocycloheptenyl, indanyl, indenyl, benzofuran-3-one, 4H-benzo[1,4]oxazine-3-one;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl;

oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl;

wherein G is substituted by one or more $R_1$, $R_2$ or $R_3$.

In another embodiment of the invention there is provided compounds of the formula(I) as described immediately above, and wherein G is phenyl, pyridinyl, pyridonyl, naphthyl, quinolinyl, isoquinolinyl, pyrazinyl, benzimidazolyl, benzoxazolyl, benzofuranyl, benzothiophenyl, benzpyrazolyl, dihydrobenzofuranyl, dihydrobenzothiophenyl, indanyl, indenyl, indolyl, indolinyl, indolonyl, indolinonyl, benzofuran-3-one or 4H-benzo[1,4]oxazine-3-one, wherein G is substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each optionally substituted by one or more $R_4$ or $R_5$ groups;

L is a:

$C_{1-4}$ saturated or unsaturated branched or unbranched carbon chain;

wherein one or more methylene groups are optionally independently replaced by heteroatoms chosen from O, N and $S(O)_m$; and wherein said L is optionally substituted with 0-2 oxo groups and one or more $C_{1-4}$ branched or unbranched alkyl optionally substituted by one or more halogen atoms;

Q is:

phenyl, naphthyl, pyridinyl or imidazolyl which are optionally substituted with one to three halogen, $C_{1-3}$ alkyl, $C_{1-3}$ alkoxy, hydroxy, amino, mono- or di-($C_{1-3}$ alkyl)amino or mono- or di-(phenyl-$C_{1-3}$ alkyl)amino;

tetrahydropyranyl, tetrahydrofuranyl, morpholino, thiomorpholino, thiomorpholino sulfoxide, piperidinyl, piperidinonyl, tetrahydropyrimidonyl, pentamethylene sulfide, pentamethylene sulfoxide or pentamethylene sulfone which are optionally substituted with one to three $C_{1-3}$ alkyl, $C_{1-3}$ alkoxy, hydroxy, mono- or di-($C_{1-3}$ alkyl) amino-$C_{1-3}$ alkyl, phenylamino-$C_{1-3}$ alkyl or $C_{1-3}$ alkoxy-$C_{1-3}$ alkyl;

each $R_1$ is independently:

$C_{3-5}$ branched or unbranched alkyl optionally partially or fully halogenated, and optionally substituted with one to three $C_{3-6}$ cycloalkyl, hydroxy, phenyl, thienyl, furyl, isoxazolyl or isothiazolyl; each of the aforementioned being optionally substituted with 1 to 5 halogen, $C_{1-3}$ alkyl which is optionally partially or fully halogenated, hydroxy, cyano or $C_{1-3}$ alkoxy optionally partially or fully halogenated;

cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, CYANO, hydroxy$C_{1-3}$alkyl or phenyl; or an analog of cyclopropyl, cyclobutyl, cyclopentanyl, cyclohexanyl, bicyclopentanyl or bicyclohexanyl wherein one to three ring methylene groups are independently replaced by O, S, CHOH, >C=O, >C=S or NH; or silyl containing three $C_{1-4}$ independently branched or unbranched alkyl groups optionally partially or fully halogenated;

each $R_3$ is independently:

hydrogen, phenyl, pyridinyl, pyrimidinyl, pyrazinyl, pyrrolyl, pyrrolylidinyl, imidazolyl or pyrazolyl, wherein each of the aforementioned is optionally substituted with one to five phenyl, naphthyl, heterocycle or heteroaryl as hereinabove described in this paragraph, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, cyano, $C_{1-3}$ alkoxy optionally partially or fully halogenated, phenyloxy, naphthyloxy, hetararyloxy or hetercylicoxy wherein the heteraryl or heterocyclic moiety is as hereinabove described in this paragraph, nitro, amino, mono- or di-($C_{1-3}$)alkylamino, phenylamino, naphthylamino, heterocyclic or heteroaryl amino wherein the heterocyclic or heteroaryl moiety is as hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N or carboxy-mono- or di-($C_{1-5}$)-alkyl-amino;

$C_{1-3}$ alkyl or $C_{1-3}$ alkoxy optionally partially or fully halogenated or optionally substituted with $R_{17}$;

Cyclopropyloxy, cyclopentyloxy or cyclohexyloxy which are optionally partially or fully halogenated and optionally substituted with one to three $C_{1-3}$ alkyl groups optionally partially or fully halogenated, wherein one to three ring methylene groups are replaced independently by O, $S(O)_m$, CHOH, >C=O, >C=S or NH;

$C_{0-6}$ branched or unbranched alkyl optionally substituted with $OR_{18}$; amino or $C_1$-$C_5$ branched or unbranched mono- or di-alkylamino optionally substituted with $R_{19}$;

$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$ alkenyl substituted by $R_{23}R_{24}NC(O)$—;

$C_{2-4}$ alkynyl branched or unbranched carbon chain optionally partially or fully halogenated and optionally independently substituted with 0-2 oxo groups, pyrroldinyl, pyrrolyl or one or more $C_{1-4}$ branched or unbranched alkyl optionally substituted by one or more halogen atoms;

X is O; and $R_{23}$ and $R_{24}$ taken together optionally form imidazole, piperidine, morpholino, piperazine or a pyridinyl ring.

In yet another embodiment of the invention there is provided compounds of the formula(I) as described immediately above, and wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl, indolinonyl, cyclopropanyl, cyclohexanyl, piperidinyl or tetrahydropyran, wherein G is substituted by one or more $R_1$, $R_2$ or $R_3$;

Ar is naphthyl;

L is a:

$C_{1-4}$ alkyl or alkynyl branched or unbranched carbon chain;

wherein one methylene group is optionally independently replaced by heteroatoms chosen from O, N and $S(O)_m$; and wherein said L is optionally substituted with 0-2 oxo groups and one or more $C_{1-2}$ alkyl optionally substituted by one or more halogen atoms;

Q is:

phenyl, pyridinyl, pyrimidinyl, imidazolyl, tetrahydropyranyl, morpholino, thiomorpholino, thiomorpholino sulfoxide, piperidinyl, piperidinonyl or pentamethylene sulfoxide which are optionally substituted with one to three amino, mono- or di-(phenyl-$C_{1-3}$ alkyl)amino, methyl, ethyl, methoxy, ethoxy, methoxymethyl or ethoxymethyl;

each $R_1$ is independently:

$C_{3-5}$ branched or unbranched alkyl optionally partially or fully halogenated, and optionally substituted with phenyl substituted with 0 to 5 halogen, $C_{1-3}$ alkyl optionally partially or fully halogenated, hydroxy, cyano or $C_{1-3}$alkoxy optionally partially or fully halogenated;

cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$alkyl or phenyl; or an analog of cyclopropyl, cyclobutyl, cyclopentanyl, cyclohexanyl, bicyclopentanyl or bicyclohexanyl wherein one ring methylene group is replaced by O; and silyl containing three $C_{1-2}$ independently branched or unbranched alkyl groups optionally partially or fully halogenated;

each $R_3$ is independently:

hydrogen, phenyl, pyridinyl, pyrimidinyl, pyrrolylidinyl, 2,5-pyrrolidin-dione, imidazolyl, pyrazolyl, each of the aforementioned is optionally substituted with one to five $C_{1-3}$ alkyl optionally partially or fully halogenated, halogen, oxo, hydroxy, cyano or $C_{1-3}$ alkoxy optionally partially or fully halogenated;

$C_{1-3}$ alkyl or $C_{1-3}$ alkoxy which may optionally be partially or fully halogenated or optionally substituted with $R_{17}$;

Cyclopropyloxy, cyclopentyloxy or cyclohexyloxy which are optionally partially or fully halogenated and optionally substituted with one to three $C_{1-3}$ alkyl groups optionally partially or fully halogenated, wherein one to three ring methylene groups are replaced independently by O, $S(O)_m$, CHOH, >C=O, >C=S or NH;

$C_{0-3}$ branched or unbranched alkyl optionally substituted with $OR_{18}$; amino or $C_1$-$C_3$ branched or unbranched mono- or di-alkylamino optionally substituted with $R_{19}$;

$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl; and $R_{23}$ and $R_{24}$ taken together optionally form morpholino.

In yet still another embodiment of the invention there is provided compounds of the formula(I) as described immediately above, and wherein G is phenyl, pyridinyl, pyridonyl, naphthyl, quinolinyl, isoquinolinyl, dihydrobenzofuranyl, indanyl, indolinyl, indolonyl, indolinonyl or cyclopropanyl, wherein G is substituted by one or more $R_1$, $R_2$ or $R_3$;

Ar is 1-naphthyl;

L is:

O—$CH_2$—, O—$CH_2CH_2$, O—$CH_2CH_2CH_2$, O—$CH_2CH_2(CH_3)$, O—$CH_2(CH_3)CH_2$, $NHCH_2$, $NHCH_2CH_2$, $NHCH_2CH_2CH_2$, $S(O)_mCH_2$, $S(O)_mCH_2CH_2$, $S(O)_mCH_2CH_2CH_2$, $CH_2CH_2$, $CH_2CH_2CH_2$, O—$CH_2C(O)$, HC≡C—$CH_2$ or HC≡C—$CH_2O$;

each $R_1$ is independently:

$C_{3-5}$ branched or unbranched alkyl optionally partially or fully halogenated, and optionally substituted with phenyl;

cyclopropyl, cyclopentanyl, cyclohexanyl or bicyclopentanyl optionally substituted with one to three methyl groups optionally be partially or fully halogenated, CYANO, hydroxymethyl or phenyl;

cyclopentyloxy or cyclohexyloxy which are optionally partially or fully halogenated; 2-tetrahydrofuranyl substituted by methyl; or trimethylsilyl;

each $R_3$ is independently:

hydrogen, phenyl, pyridinyl, pyrimidinyl, pyrrolylidinyl, 2,5-pyrrolidin-dione, imidazolyl or pyrazolyl, wherein each of the aforementioned is optionally substituted with $C_{1-2}$ alkyl optionally partially or fully halogenated;

$C_{1-3}$ alkyl or $C_{1-3}$ alkoxy each optionally partially or fully halogenated or optionally substituted with diethylamino;

$C_{0-3}$ branched or unbranched alkyl optionally substituted with $OR_{18}$;

amino or $C_1$-$C_3$ branched or unbranched mono- or di-alkylamino optionally substituted with $R_{19}$;

$CH_3C(O)NH$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl;

$R_{23}$ and $R_{24}$ are H or $R_{23}$ and $R_{24}$ taken together optionally form morpholino; and $R_{26}$ is morpholino.

In another embodiment of the invention there is provided of the formula(I) as described immediately above, and wherein G is phenyl substituted by one or more $R_1$, $R_2$ or $R_3$; and L is:

O, NH, $CH_2$ or $S(O)_m$.

In yet another embodiment of the invention there is provided of the formula(I) as described in the fourth embodiment above, and wherein G is phenyl or pyridinyl substituted by one or more $R_1$, $R_2$ or $R_3$;

Ar is 1-naphthyl;

L is:

$C(O)CH_2$—, >$C(O)$, O, or $CH_2$;

each $R_1$ is independently:

$C_{3-5}$ branched or unbranched alkyl optionally partially or fully halogenated, and each $R_3$ is independently:

hydrogen, $C_{1-3}$ alkyl or $C_{1-3}$ alkoxy each optionally be partially or fully halogenated or optionally substituted with diethylamino;

$CH_3C(O)NH$—, $R_{22}O$—; $R_{23}R_{24}NC(O)$—; $R_{26}C(O)N(R_{21})$— or $R_{26}C(O)CH_2N(R_{21})$—;

$R_{23}$ and $R_{24}$ are H or $R_{23}$ and $R_{24}$ taken together optionally form morpholino; and $R_{26}$ is alkylamino mono- or di-$C_{0-4}$ branched or unbranched.

In another embodiment of the invention there is provided of the formula(I) as described immediately above, and wherein G is pyridinyl and L is C(O)CH$_2$—, >C(O), O or CH$_2$.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

All terms as used herein in this specification, unless otherwise stated, shall be understood in their ordinary meaning as known in the art. For example, "C$_{1-4}$alkoxy" is a C$_{1-4}$alkyl with a terminal oxygen, such as methoxy, ethoxy, propoxy, and butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Preferred heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl.

The term "heteroaryl" shall be understood to mean an aromatic 5-8 membered monocyclic or 8-11 membered bicyclic ring containing 1-4 heteroatoms chosen from N, O and S. Such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl.

The term "heteroatom" as used herein shall be understood to mean atoms other than carbon such as O, N, S and P.

The term "aryl" as used herein shall be understood to mean aromatic carbocycle or heteroaryl as defined herein.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the formula (I) capable of being metabolized enzymatically or chemically. This includes, for example, hydroxylated or oxidized derivative compounds of the formula (I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—(C$_1$—C$_4$ alkyl)$_4$$^+$ salts.

In addition, the compounds of this invention include prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of formula (I), thereby imparting the desired pharmacological effect.

METHODS OF USE

In accordance with the invention, there are provided methods of using the compounds of the formula (I). The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula (I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

GENERAL SYNTHETIC METHODS

The invention additionally provides for methods of making the compounds of the formula (I). In all schemes "G" in the formulas shown below shall have the meaning of "G" in the formula (I) of the invention described hereinabove.

The compounds of the invention may be prepared by Method A, B, C or D as illustrated in Scheme I, preferably method C.

Scheme I

Method A

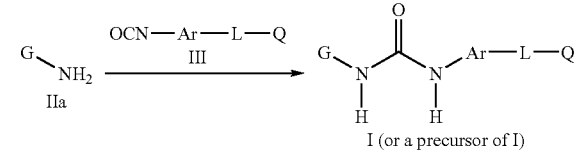

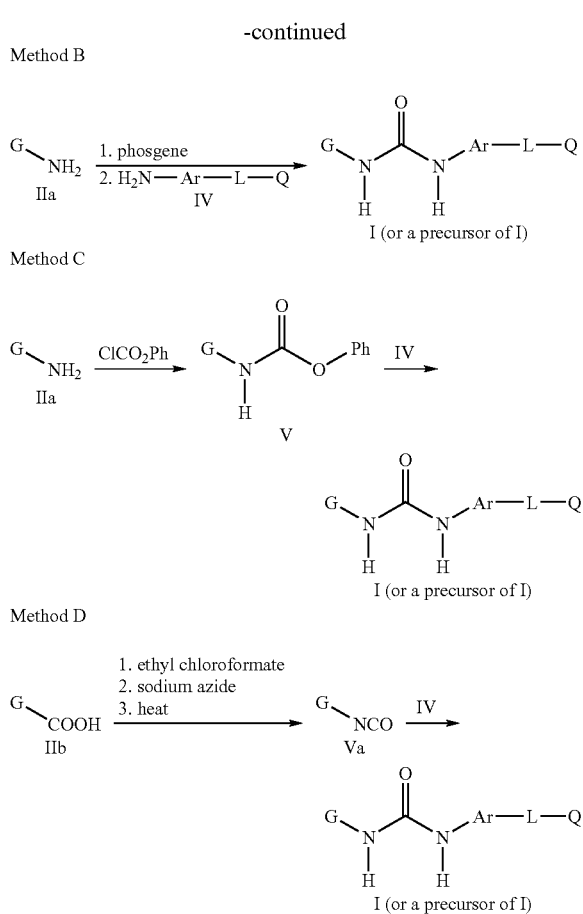

In Method A, a mixture of an arylamine of formula IIa and an arylisocyanate of formula III is dissolved in a non-protic, anhydrous solvent such as THF, ether, toluene, dioxane or ethyl acetate. The preferred solvent is THF. The mixture is stirred at between 0-45° C., preferably at 25° C., for 2-24 h, and the volatiles are removed. Purification of the residue can be accomplished by recrystallization from an appropriate solvent such as ethyl acetate/hexanes, ethyl acetate/methanol, THF/petroleum ether or ethanol/water or by silica gel chromatography, using for example, hexanes and ethyl acetate as eluents, providing the product of formula I or precursors thereof.

In Method B, an arylamine of formula IIa is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5-30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0-45° C., preferably at 25° C., for 2-24 h, and the volatiles are removed. Purification of the residue by recrystallization or by silica gel chromatography, as above, provides the product of formula I or precursors thereof.

In Method C, an arylamine of formula IIa is dissolved in a suitable halogenated solvent such as methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0-85° C., preferably at reflux temperature, for 2-24 h, and the volatiles are removed providing carbamate V. The carbamate and arylamine IV are mixed in a non-protic, anhydrous solvent such as THF, ether, toluene, dioxane, methylene chloride or ethyl acetate. The preferred solvent is THF. The mixture is stirred at between 0-110° C., preferably at reflux temperature, for 2-24 h, and the volatiles are removed. Purification of the residue as above provides the product of formula I or precursors thereof.

In Method D, an aromatic carboxylic acid is dissolved in a non-protic solvent, such as THF or diethyl ether, and an inorganic base, such as triethyl amine is added and the mixture is cooled to −30-0° C., with the preferred temperature being −10° C. An alkyl chloroformate, such as ethyl chloroformate, is added dropwise and the resulting mixture stirred at below room temperature, such as 0° C. for 1-3 hours. A solution of sodium azide in water is added and the mixture stirred between 1-3 hours, diluted with toluene and the organic layer dried and reduced in volume. This mixture is heated at reflux for 1-4 hours, cooled to room temperature to give isocyanate (Vb) which can be reacted with amine (IV) to give product of formula I or precursors thereof.

Method E describes a procedure by which one may obtain a product of formula (I) in which Ar is tetrahydroquinoline. Preparations of tetrahydroquinoline intermediates that may be used are known in the art (see for example C. Wang et al., *Biorg. Med. Chem. Lett.,* 1998, 2685; W. S. Johnson and B. G. Buell, *J. Am. Chem. Soc.,* 1952, 74, 4513; P. D. Leeson et al., *Med. Chem. Res.,* 1991, 1, 64; A. L. Tokes, *Synth. Commun.,* 1989, 19, 2081; U. Gerlach et al., EP 0 857 724 A1, May 2, 1998). The following method is illustrative.

Aniline is reacted with an acrylate ester such as t-butyl acrylate, in a suitable solvent such as acetic acid at reflux temperature. The product obtained is cyclized by heating under acidic conditions, such as heating in polyphosphoric acid to give the cyclic ketone. The ketone is reduced with a suitable reducing agent such as NaBH4 to give the corresponding alcohol. The alcohol is converted to the amine by methods known in the art, for example, reaction with sodium azide under anhydrous acidic conditions in ethereal solvent provides the azide. Protection of the tetrahydroquinoline nitrogen, for example by treatment with t-butyl dicarbonate under heating conditions affords the t-boc protected compound. Reaction under suitable reducing conditions, for example, Pd/charcoal and $H_2$ gas affords the t-boc protected 4-amino tetrahydroquinoline.

This may then be reacted using the desired Method B, C or D, to provide the urea. Deprotection, for example with trifluoroacetic acid, can be followed by further reaction to add L-Q to provide the desired product of formula (I). For example, treatment with the desired acid, such as 4-pyridine acetic acid hydrochloride in the presence of a suitable carbodiimide coupling reagent provides an amide. Reaction with an arylaldehyde, for example 3,5-dimethoxybenzaldehyde in the presence of a suitable reducing agent such as $Na(AcO)_3BH$ at room temperature affords the tetrahydroquinoline product in which L is a methylene bridge and Q is a substituted aryl group.

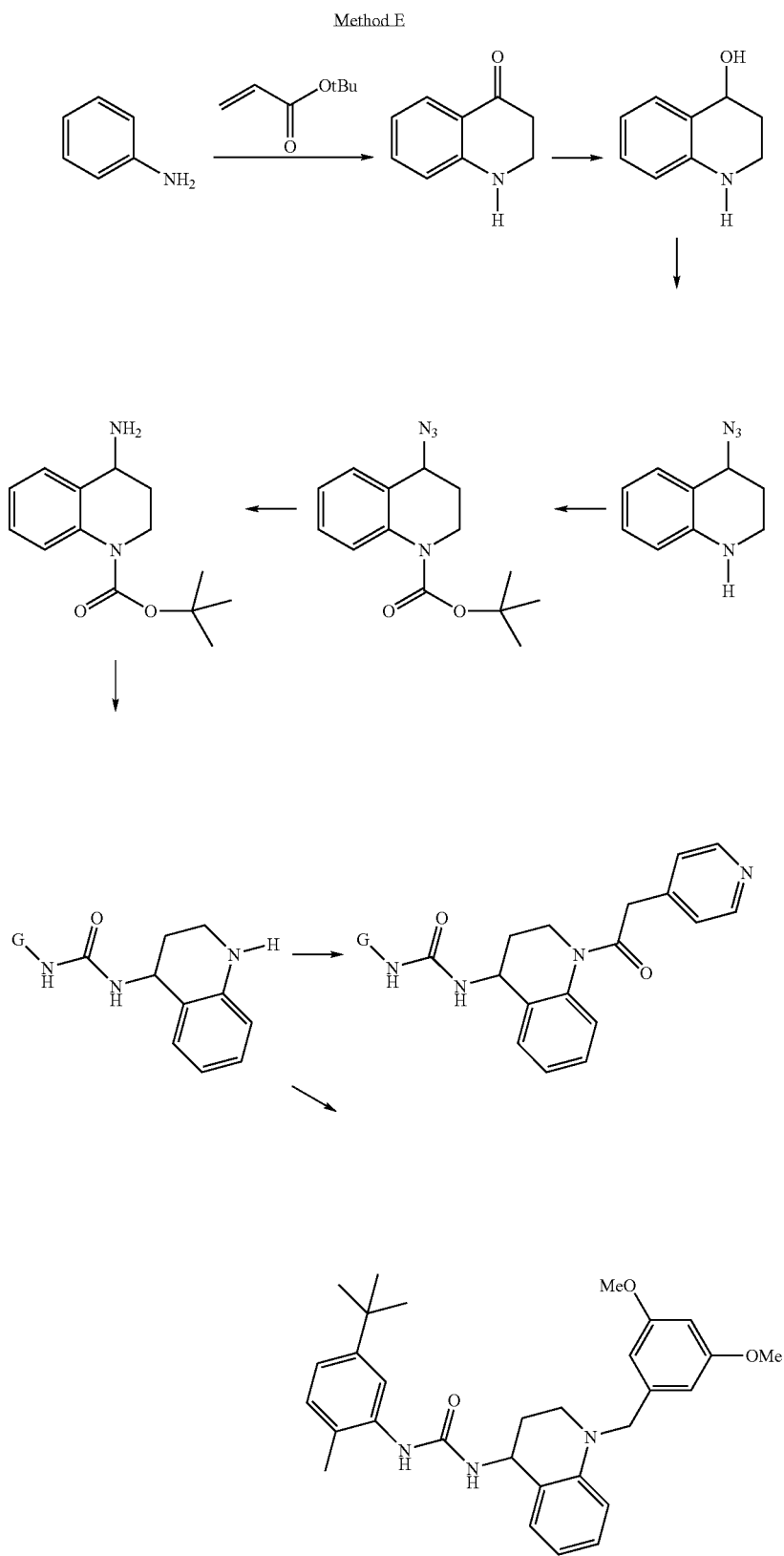

EXPERIMENTAL SECTION

Arylamine intermediates of formula IIa are either commercially available or may be prepared by methods known to those skilled in the art. Examples 1-5 (Methods F-J) are representative of procedures for preparing aryl amine or aryl isocyanate derivatives that may be used in Methods A-D. It will be obvious to those skilled in the art that other desired intermediates could be made by these methods by using appropriately substituted starting materials and intermediates.

Example 1

(Method F): Synthesis of 5-tert-butyl-2-methylaniline

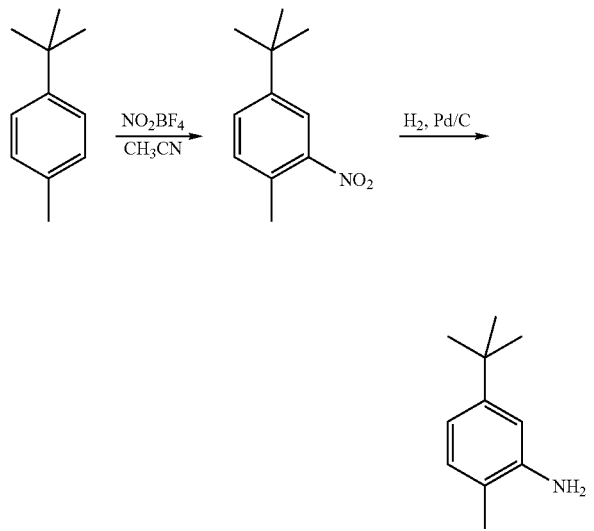

To a solution of 4-tert-butyl toluene (5 g, 33.7 mmol) in acetonitrile (150 mL) at 0° C. was added nitronium tetrafluoroborate (5.83 g, 40.5 mmol). After 30 min at room temperature, the reaction was diluted with water (50 mL) and extracted with ethyl acetate (3×30 mL). The combined organic extracts were washed with brine and dried (MgSO$_4$). Removal of the volatiles in vacuo left a residue which was purified by flash chromatography using 10% methylene chloride in petroleum ether as eluent. Concentration in vacuo of the product rich fractions provided 3.8 g of 4-tert-butyl-2-nitrotoluene.

4-tert-Butyl-2-nitrotoluene (200 mg, 1.1 mmol) was dissolved in DMF (10 mL). The catalyst (10% Pd/C, 5 mg) was added and the system was purged with argon then exposed to H$_2$ (1 atm) for 12 h. The mixture was filtered over a pad of diatomaceous earth and the filtrate was diluted with water and extracted with ethyl acetate (3×10 mL). The combined organic extracts were washed with brine and dried (MgSO$_4$). Removal of the volatiles in vacuo provided the product 5-tert-butyl-2-methylaniline.

Example 2

(Method G): Synthesis of 6-tert-butyl-2-chloro-3-methylpyridin-yl-isocyanate

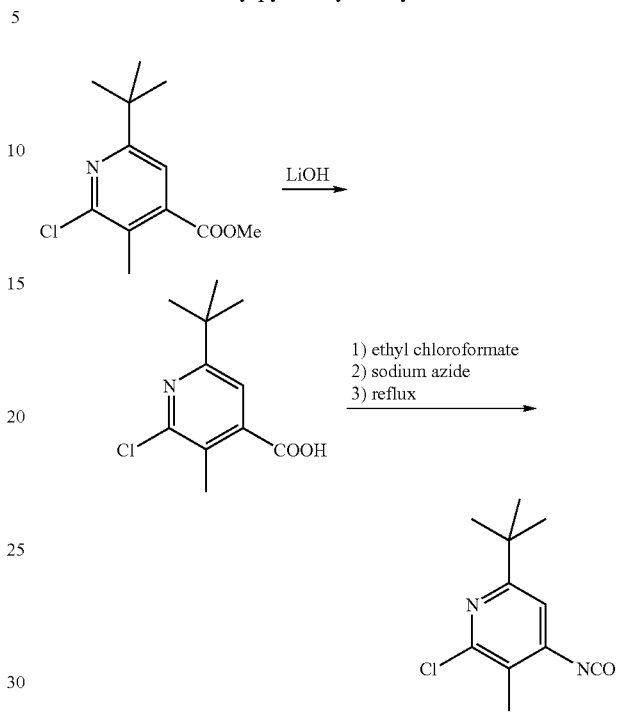

A mixture of 2-t-butyl-6-chloro-5-methylpyridine-4-carboxylic acid methyl ester (2.27 g, 9.39 mmol) and LiOH monohydrate (2.36 g, 56.3 mmol) in methanol (30 mL) and water (10 mL) was stirred at room temperature for 24 h. Removal of the volatiles in vacuo provided a residue which was purified by chromatography on silica gel using 5% TFA in dichloromethane as the eluent. Concentration in vacuo of the product rich fractions provided the corresponding carboxylic acid (1.41 g, 66.3%).

To a stirred solution of the above carboxylic acid (0.54 g, 2.36 mmol) and triethylamine (0.66 mL, 4.75 mmol) in THF (6 mL) at −10° C. ethyl chloroformate (0.34 mL, 3.51 mmol) was added dropwise. The resulting mixture was stirred at 0° C. for 1 h. A solution of sodium azide (0.40 g, 6.0 mmol) in water (2 mL) was added and stirring was continued for another 1 h. The mixture was extracted with toluene. The organic phase was separated, dried with sodium sulfate, and reduced in volume to 15 mL and heated at reflux for 2 h to provide 6-tert-butyl-2-chloro-3-methylpyridin-yl-isocyanate which was used without further purification.

Example 3

(Method H): Synthesis of 5-tert-butyl-2-(1H-pyrazol-4-yl)aniline

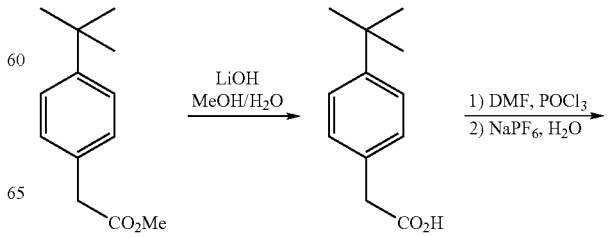

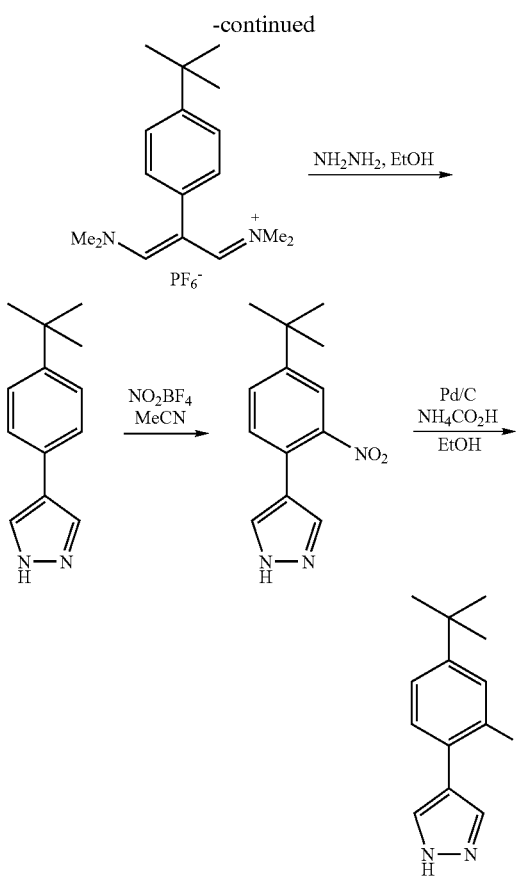

The organic layers were combined, dried (MgSO$_4$) and the volatiles removed in vacuo. Purification of the yellow oil by silica gel chromatography using 60% CH$_2$Cl$_2$ in ethyl acetate as the eluent and concentration in vacuo of the product rich fractions gave 4-(4-t-butyl-2-nitrophenyl)pyrazole as a yellow crystalline solid (71 mg, 58%).

A mixture of 4-(4-t-butyl-2-nitrophenyl)pyrazole (0.27 mmol), 10% Pd/C (0.2 eq by weight of nitro compound) and NH$_4$CO$_2$H (2.7 mmol) in ethanol (3 mL) was stirred for 30 min and filtered through a bed of diatomaceous earth. The filtrate was concentrated under reduced pressure and the residue dissolved in water. The solid was filtered, washed with water and dried to give the product (54 mg, 93%).

Example 4

(Method I): Synthesis of 5-tert-butyl-2-(morpholin-4-yl)aniline

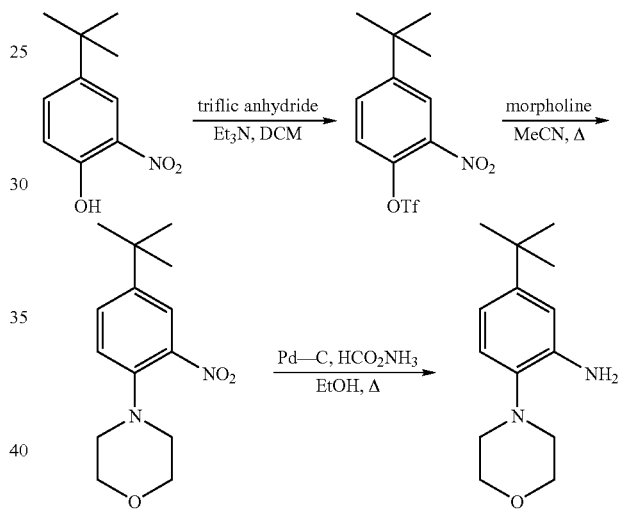

Methyl 4-t-butylphenylacetate (20 mmol) was dissolved in MeOH (160 mL) and treated with water (40 mL) and LiOH monohydrate (30 mmol). The reaction was allowed to stir at room temperature overnight. The volatiles were removed under reduced pressure and the remaining residue was diluted with water and neutralized to pH 4 with 1 N sulfuric acid. The resulting solids were filtered, washed with water and dried to leave 4-t-butylphenylacetic acid as an off-white solid (3.8 g, 99%).

Anhydrous DMF (139 mmol) was cooled to 0° C. and treated with POCl$_3$ (79.6 mmol). After 5 min, 4-t-butylphenylacetic acid (19.9 mmol) was added and the mixture heated at 110° C. for 2 h, cooled to room temperature and poured into a stirred solution of NaPF$_6$ (19.8 mmol) in water (200 mL). The solid was filtered, washed with water, and dried (7.8 g, 97%).

A mixture of the above salt (5 mmol) and hydrazine hydrate (5 mmol) in EtOH (50 mL) was heated at 90° C. for 2 h and cooled to room temperature. The volatiles were removed under reduced pressure and the remaining residue diluted with ice water. The solids were filtered, washed with water and dried providing 4-(4-t-butylphenyl)pyrazole (973 mg, 97%).

To a mixture of 4-(4-t-butylphenyl)pyrazole (0.5 mmol) in MeCN (2 mL) at 0° C. was added NO$_2$BF$_4$ (0.6 mmol). The mixture was allowed to warm slowly to room temperature, stirred for 2 h and quenched with aqueous NaHCO$_3$. The volatiles were removed under reduced pressure. The residue was diluted with water and extracted with CH$_2$Cl$_2$.

To a mixture of 2-nitro-4-tert-butyl phenol (5.4 g, 0.027 mol) and Et$_3$N (5.85 mL, 0.042 mol) in methylene chloride (100 mL) at 0° C., triflic anhydride (5.2 mL, 0.030 mol) was added via addition funnel. The reaction was stirred at room temperature for 2 days, diluted with water (10 mL) and extracted with ethyl acetate (3×10 mL). The combined organic extracts were washed with brine and dried (MgSO$_4$). Removal of the volatiles in vacuo afforded 8.8 g (97% yield) of trifluoromethanesulfonic acid 4-tert-butyl-2-nitro-phenyl ester, which crystallized in air.

A mixture of (400 mg, 1.2 mmol) of the above triflate and morpholine (314 mL, 3.6 mmol) in acetonitrile (10 mL) was stirred at 80° C. for 4 h. Removal of the of volatiles in vacuo afforded 315 mg, 97% yield of 4-(4-tert-butyl-2-nitrophenyl)morpholine, as a yellow solid.

A mixture of the above nitro compound (320 mg, 1.2 mmol), ammonium formate (460 mg, 7.3 mmol) and 10% Pd/C (5 mg) in ethanol (20 mL) was stirred at 100° C. for 1 h, cooled to room temperature and filtered. Removal of the volatiles in vacuo provided 260 mg (93%) of the title compound.

Example 5

(Method J): Synthesis of 3-bromo-5-tert-butyl-2-[2-(morpholin-4-yl)ethylamino]aniline

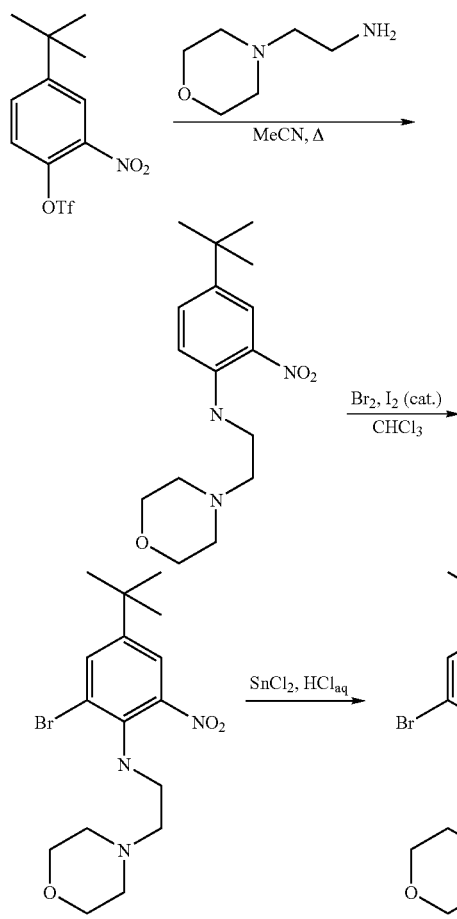

A mixture of trifluoromethanesulfonic acid 4-tert-butyl-2-nitro-phenyl ester (400 mg, 1.2 mmol) and N-(2-aminoethyl)morpholine (481 μL, 3.7 mmol) in acetonitrile (10 mL) was stirred at 80° C. for 4 h and cooled to room temperature. Removal of the volatiles in vacuo provided a residue that was purified by flash chromatography using 15% ethyl acetate in petroleum ether as eluent. Concentration in vacuo of the product-rich fractions provided 340 mg, 90% yield of the desired product, 4-tert-butyl-2-nitro-N-[2-(morpholin-4-yl)ethyl]aniline To a solution of 4-tert-butyl-2-nitro-N-[2-(morpholin-4-yl)ethyl]aniline (240 mg, 0.8 mmol) in chloroform (1 mL) was added bromine (42 μL, 0.8 mmol) and an iodine crystal. The mixture was stirred at room temperature for 1 h, diluted with water (10 mL) and extracted with ethyl acetate (3×10 mL). The combined organic extracts were washed with brine and dried (MgSO$_4$). Removal of the volatiles in vacuo afforded 300 mg, 99% yield of the desired aryl bromide, 6-bromo-4-tert-butyl-2-nitro-N-[2-(morpholin-4-yl)ethyl]aniline To a solution of 6-bromo-4-tert-butyl-2-nitro-N-[2-(morpholin-4-yl)ethyl]aniline (300 mg, 0.7 mmol) in 6 N HCl (15 mL) at 0° C. was added stannous chloride (990 mg, 4.4 mmol), as a solution in 6N HCl (5 mL). The reaction was stirred for 1 h, basified with 20% potassium hydroxide and extracted with ethyl acetate (3×10 mL). The combined organic extracts were washed with brine and dried (MgSO$_4$). Removal of the volatiles in vacuo provided 200 mg, 72% yield, of the desired amine.

Examples 6-9 (Methods K-N) are representative procedures for the preparation of intermediates of formula IV which may be used in Methods B-D (Scheme I). The preparation of intermediates of formula IV may also be made with known starting materials and by methods known to those skilled in the art including those to be found in U.S. Ser. No. 09/484,638 incorporated herein by reference.

Example 6

(Method K): Synthesis of 1-amino-4-(2-morpholin-4-yl-ethoxy)naphthalene

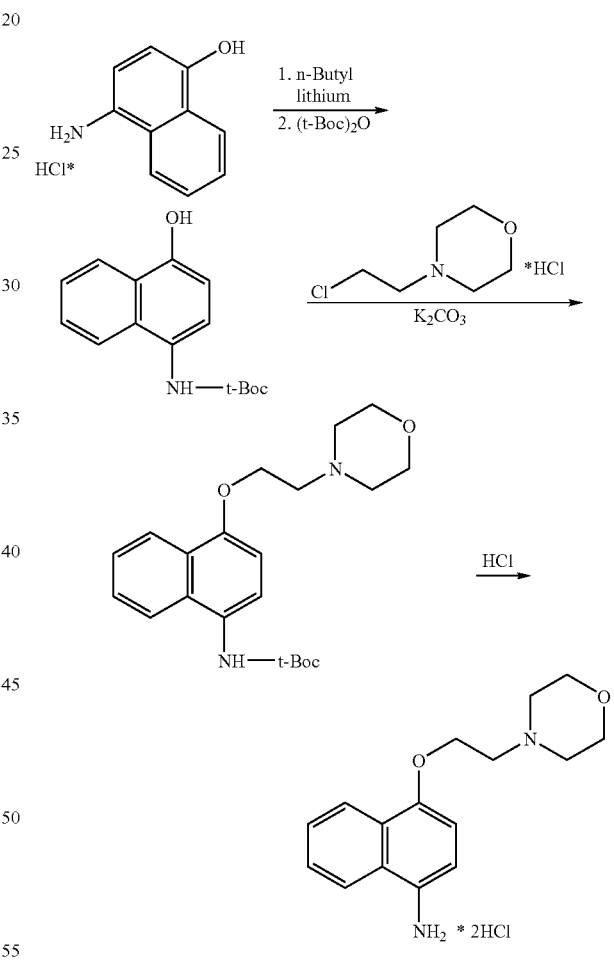

To a mixture of 4-amino-1-naphthol hydrochloride (172.1 g) in 750 mL anhydrous THF at −78° C. was added dropwise over 60 min n-butyl lithium (490 mL of a 1.60 M solution in hexanes). After the addition was complete the mixture was allowed to warm to room temperature and then cooled to −78° C. and di-tert-butyl dicarbonate [(t-Boc)$_2$O, 192 g] in 200 mL THF was added over 20 min. The mixture was slowly warmed to room temperature and stirred for 3 h and most of the volatiles removed in vacuo. The residue was diluted with ethyl acetate (1 L) and washed with water (2×200 mL) and brine (200 mL) and filtered through diatomaceous earth and dried (MgSO$_4$). Removal of the volatiles in vacuo provided the N-t-Boc protected derivative (226.1 g).

A mixture of the above N-t-Boc derivative (0.464 g), 4-(2-chloroethyl)morpholine hydrochloride (0.3435 g) and powdered potassium carbonate (0.93 g) was heated in acetonitrile (15 mL) at 80° C. for 3 h, cooled to room temperature and diluted with ethyl acetate and water. The organic layer was washed with water, brine, dried (MgSO$_4$) and the volatiles removed in vacuo. Purification of the residue by flash chromatography using 12% hexanes in ethyl acetate as the eluent and concentration in vacuo of the product-rich fractions afforded N-t-Boc-4-[2-(morpholin-4-yl)ethoxy] napth-1-yl-amine. A solution of this intermediate (0.511 g) and HCl (1 mL of 4M HCl in dioxane solution) in 5 mL dioxane was stirred at room temperature for 20 h. Removal of the volatiles in vacuo provided 4-[2-(morpholin-4-yl) ethoxy]napth-1-yl-amine.

Example 7

(Method L): Synthesis of 1-amino-4-(4-pyridinyl)oxynaphthalene

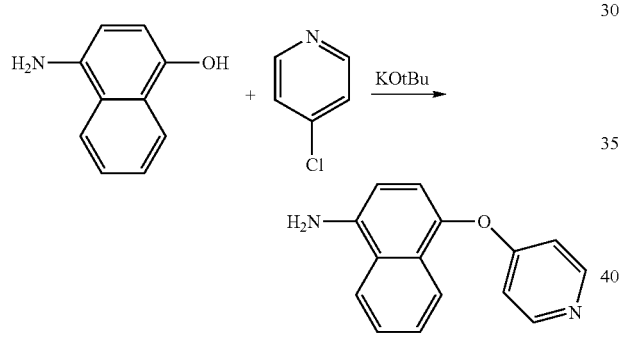

To a stirred mixture of 4-amino-1-naphthol hydrochloride (2.5 g, 12.8 mmol) and 4-chloropyridine hydrochloride (3.84 g, 29.2 mmol) in NMP (20 ml) was added potassium tert-butoxide (6.0 g, 53.47 mmol) slowly. The mixture was heated at 120° C. for 6 h, cooled to room temperature and diluted with water and dichloromethane. The combined organic extracts were washed with HCl (2N), saturated aqueous NaHCO$_3$ and brine and dried (Na$_2$SO$_4$). Removal of the volatiles in vacuo afforded the product (0.5 g, 16%).

Example 8

(Method M): Synthesis of 1-amino-4-(3-(tetrahydropyran-2-yl-oxy)propyn-1-yl)naphthalene

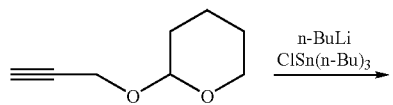

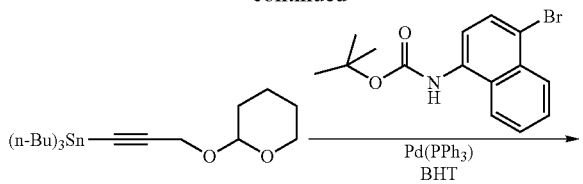

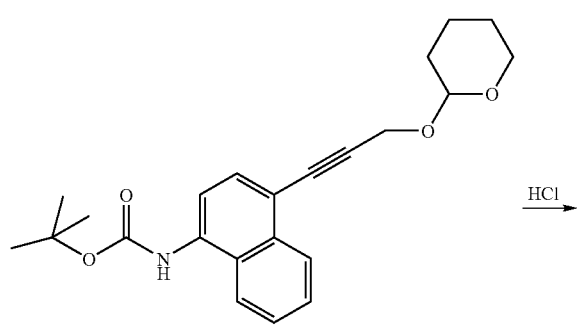

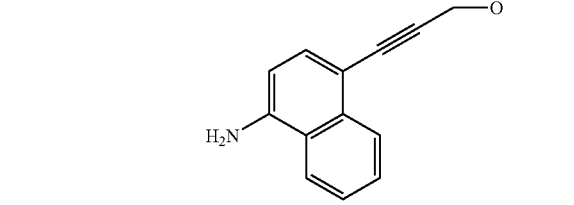

To a solution of tetrahydro-2-(2-propynyloxy)-2H-pyran in anhydrous THF at −78° C. under inert atmosphere n-butyllithium (1.1 molar equivalents) was added via syringe. After 1 h stirring at −78° C., tributyltin chloride (1 molar equivalent) was added and the cooling bath was removed. After stirring at ambient temperature for 1 h the reaction mixture was quenched with saturated NH$_4$Cl solution and extracted with ethyl ether. The combined ethereal extracts were washed with brine and dried (MgSO$_4$). After filtration all volatiles were removed in vacuo to produce the alkynyl tri-n-butylstannane as a yellow oil which was used without further purification.

A mixture of N-t-Boc-4-bromonaphthylamine and the above alkynyl stannane (1.5 molar equivalents) and BHT (20% weight equivalent) in toluene were heated at reflux under inert atmosphere and treated with palladium (0) tetrakis-(triphenylphosphine) (0.1 molar equivalent) When the reaction was complete, as judged by the color change to black, it was cooled to room temperature. An aqueous solution of KF (5M) was added and the mixture was stirred vigorously for 6 h and extracted with ethyl acetate. The combined organic extracts were washed with brine and dried (MgSO$_4$), filtered and all volatiles were removed in vacuo. Purification of the residue by column chromatography afforded the N-t-Boc intermediate. Removal of the N-t-Boc protecting group with HCl in dioxane provided the amino intermediate.

Example 9

(Method N): Synthesis of 1-amino-4-[2-(2-phenoxymethylmorpholin-4-yl)-ethoxy]naphthalene dihydrochloride

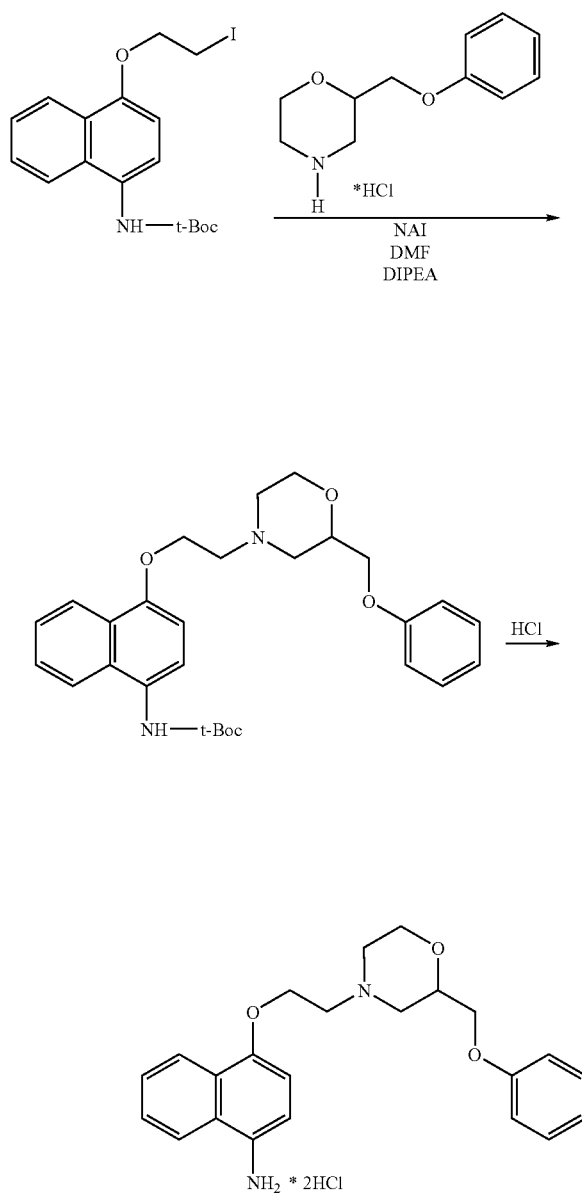

A solution of 2-phenoxymorpholine hydrochloride (0.098 g), N,N-di-iso-propylethylamine (DIPEA) (149 uL), sodium iodide (0.32 g) and 1-N-Boc-4-(2-iodoethoxy)naphthylamine (0.176 g) in anhydrous DMF (1.5 mL) was heated at 40° C. overnight, cooled to room temperature and diluted with ethyl acetate and water. The organic layer was washed with water and brine and dried (MgSO$_4$). Removal of the volatiles in vacuo provided a residue that was purified by silica gel chromatography using 33% hexanes in ethyl acetate as the eluent. Concentration of the product rich fractions in vacuo furnished 1-N-Boc-4-[2-(2-phenoxymethylmorpholin-4-yl)-ethoxy]naphthylamine.

To a solution of the above t-Boc protected naphthylamine (0.18 g) in dioxane (1 mL) was added HCl (0.47 mL of a 4N HCl in dioxane solution) and the mixture stirred overnight at room temperature, diluted with ether and cooled. The solid was filtered and washed with ether and dried to provide 1-amino-4-[2-(2-phenoxymethylmorpholin-4-yl)-ethoxy] naphthalene dihydrochloride.

Urea bond formation by Methods A-D is generally known in the art. A representative example is given below.

Example 10

(Method B): 1-[5-tert-butyl-2-methylphenyl]-3-[4-(2-morpholin-4-yl-ethoxy)-naphthalen-1-yl]-urea

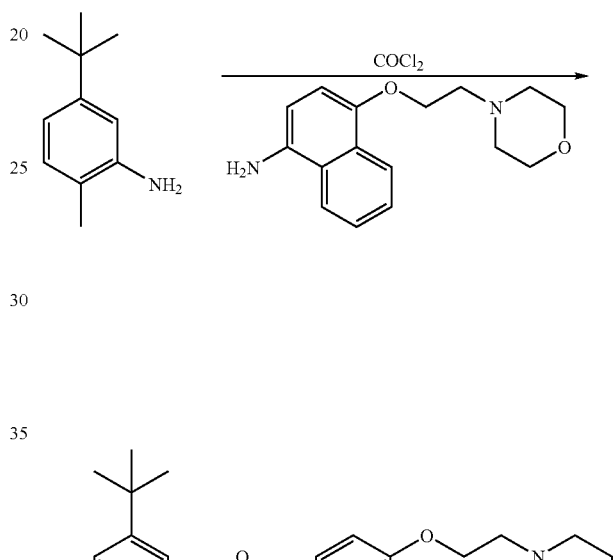

4-[2-(Morpholin-4-yl)ethoxy]napth-1-yl-amine (280 mg, 1.0 mmol) was dissolved in dichloromethane (15 mL). An equal volume of sat. aqueous sodium bicarbonate was added, and the biphasic solution was cooled to 0° C. During the addition of phosgene (1.93 M in toluene, 1.0 mL), stirring was stopped. Immediately afterward, stirring was resumed for 15 min with the reaction mixture at 0° C. The layers were separated, the organics were dried over solid magnesium sulfate and concentrated to approximately 5 mL of solution. 5-tert-Butyl-2-methylaniline (150 mg, 0.9 mmol) in dichloromethane (5 mL) was added, and the reaction mixture was stirred for 17 h at ambient temperature. The desired compound was obtained after treatment of the reaction mixture with petroleum ether and filtering to collect the precipitate (180 mg, 42%).

From the synthetic schemes and the example described above, the following representative compounds of the formula(I) can be made:

TABLE I

| Structure | Chemical Name |
|---|---|
| 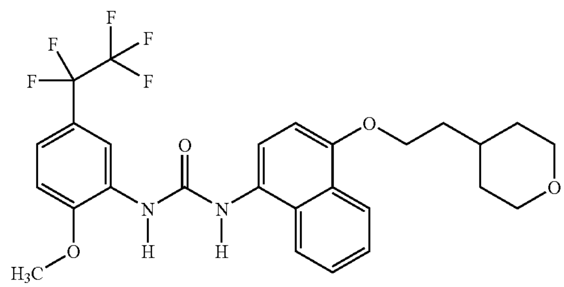 | 1-(2-Methoxy-5-pentafluoroethyl-phenyl)-3-{4-[2-(tetrahydro-pyran-4-yl)-ethoxy]-naphthalen-1-yl}-urea |
| 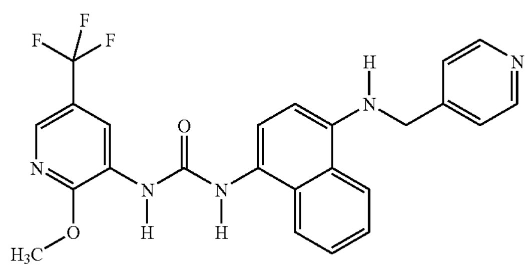 | 1-(2-Methoxy-5-trifluoromethyl-pyridin-3-yl)-3-{4-[(pyridin-4-ylmethyl)-amino]-naphthalen-1-yl}-urea |
| 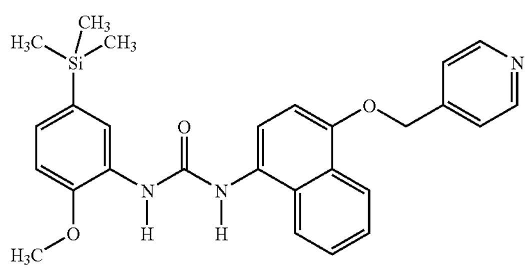 | 1-(2-Methoxy-5-trimethylsilanyl-phenyl)-3-[4-(pyridin-4-ylmethoxy)-naphthalen-1-yl]-urea |
| 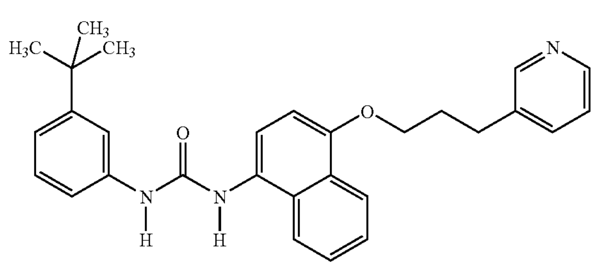 | 1-(3-tert-Butyl-phenyl)-3-[4-(3-pyridin-3-yl-propoxy)-naphthalen-1-yl]-urea |
| 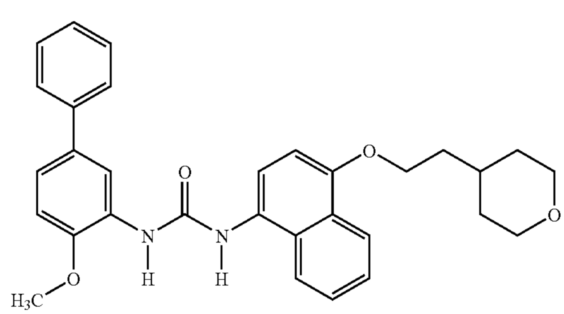 | 1-(4-Methoxy-biphenyl-3-yl)-3-{4-[2-(tetrahydro-pyran-4-yl)-ethoxy]-naphthalen-1-yl}-urea |

TABLE I-continued

| Structure | Chemical Name |
|---|---|
| 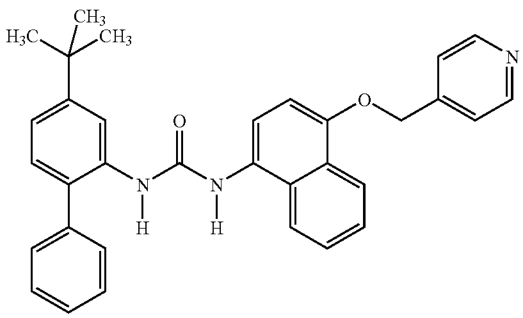 | 1-(4-tert-Butyl-biphenyl-2-yl)-3-[4-(pyridin-4-ylmethoxy)-naphthalen-1-yl]-urea |
| 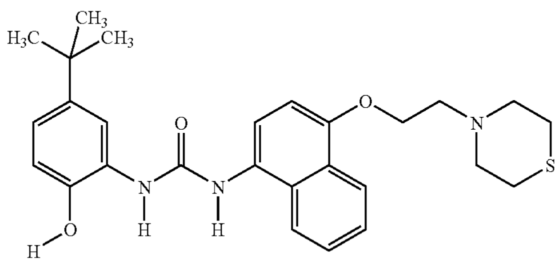 | 1-(5-tert-Butyl-2-hydroxy-phenyl)-3-[4-(2-thiomorpholin-4-yl-ethoxy)-naphthalen-1-yl]-urea |
| 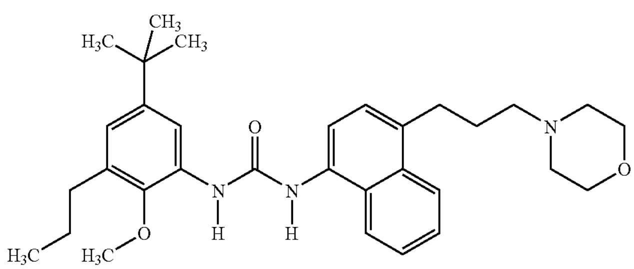 | 1-(5-tert-Butyl-2-methoxy-3-propyl-phenyl)-3-[4-(3-morpholin-4-yl-propyl)-naphthalen-1-yl]-urea |
| 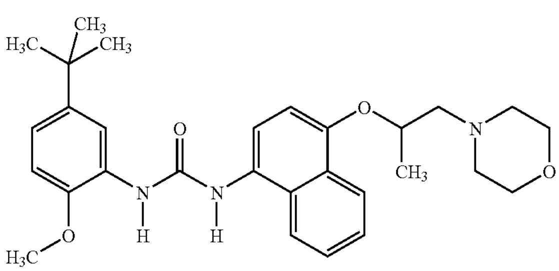 | 1-(5-tert-Butyl-2-methoxy-phenyl)-3-[4-(1-methyl-2-morpholin-4-yl-ethoxy)-naphthalen-1-yl]-urea |
| 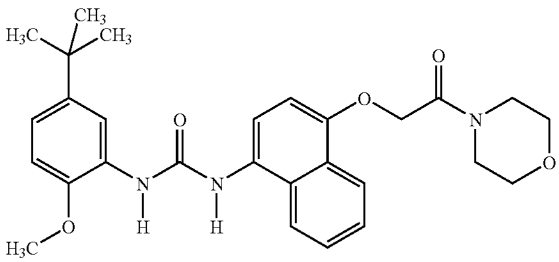 | 1-(5-tert-Butyl-2-methoxy-phenyl)-3-[4-(2-morpholin-4-yl-2-oxo-ethoxy)-naphthalen-1-yl]-urea |

TABLE I-continued

| Structure | Chemical Name |
|---|---|
| 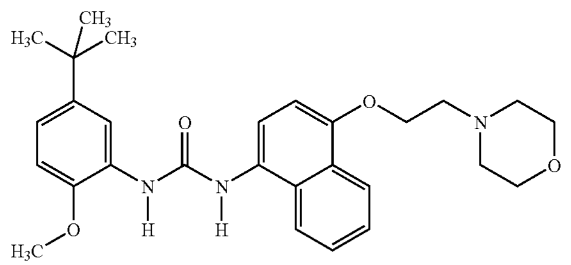 | 1-(5-tert-Butyl-2-methoxy-phenyl)-3-[4-(2-morpholin-4-yl-ethoxy)-naphthalen-1-yl]-urea |
| 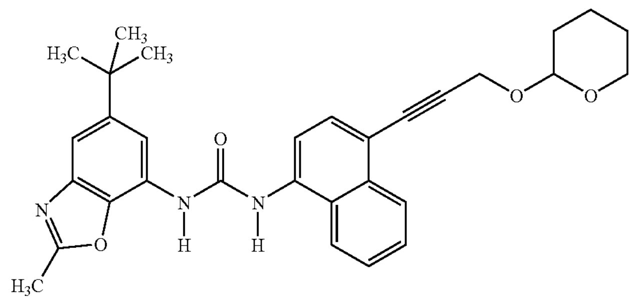 | 1-(5-tert-Butyl-2-methyl-benzooxazol-7-yl)-3-{4-[3-(tetrahydro-pyran-2-yloxy)-prop-1-ynyl]-naphthalen-1-yl}-urea |
| 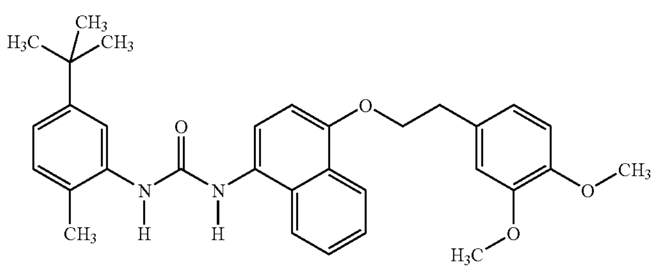 | 1-(5-tert-Butyl-2-methyl-phenyl)-3-{4-[2-(3,4-dimethoxy-phenyl)-ethoxy]-naphthalen-1-yl}-urea |
| 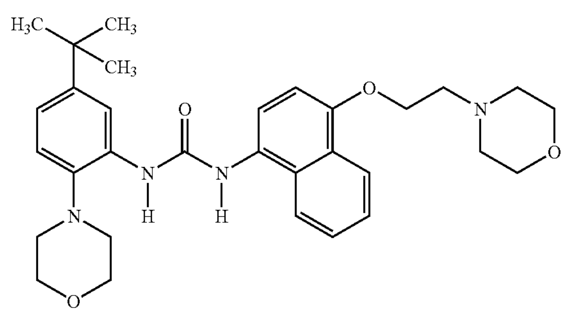 | 1-(5-tert-Butyl-2-morpholin-4-yl-phenyl)-3-[4-(2-morpholin-4-yl-ethoxy)-naphthalen-1-yl]-urea |
| 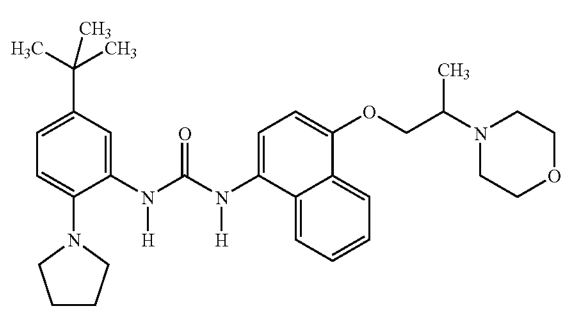 | 1-(5-tert-Butyl-2-pyrrolidin-1-yl-phenyl)-3-[4-(2-morpholin-4-yl-propoxy)-naphthalen-1-yl]-urea |

TABLE I-continued

| Structure | Chemical Name |
|---|---|
| 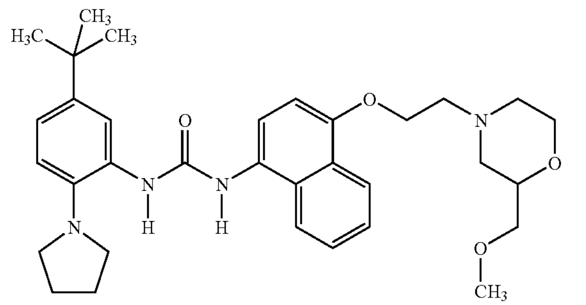 | 1-(5-tert-Butyl-2-pyrrolidin-1-yl-phenyl)-3-{4-[2-(2-methoxymethyl-morpholin-4-yl)-ethoxy]-naphthalen-1-yl}-urea |
| 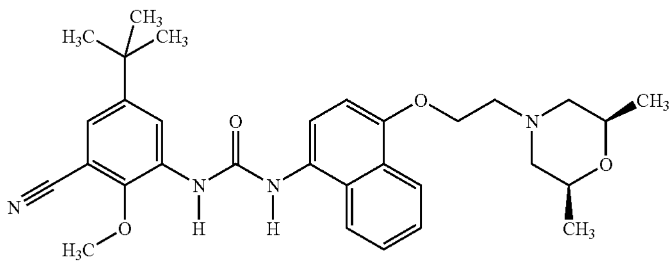 | 1-(5-tert-Butyl-3-cyano-2-methoxy-phenyl)-3-{4-[2-(2,6-dimethyl-morpholin-4-yl)-ethoxy]-naphthalen-1-yl}-urea |
| 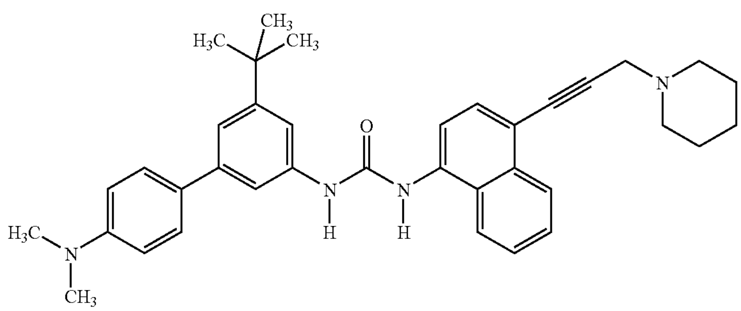 | 1-(5-tert-Butyl-4'-dimethylamino-biphenyl-3-yl)-3-[4-(3-piperidin-1-yl-prop-1-ynyl)-naphthalen-1-yl]-urea |
| 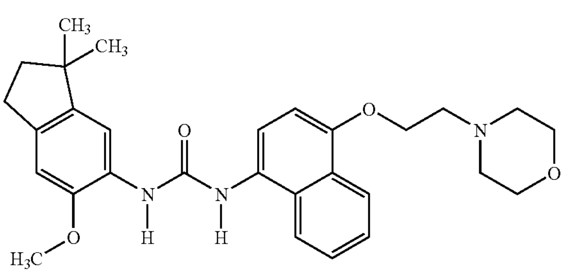 | 1-(6-Methoxy-3,3-dimethyl-indan-5-yl)-3-[4-(2-morpholin-4-yl-ethoxy)-naphthalen-1-yl]-urea |
| 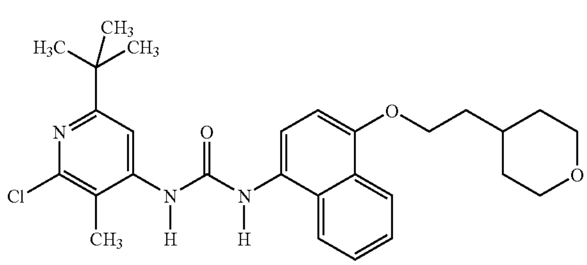 | 1-(6-tert-Butyl-2-chloro-3-methyl-pyridin-4-yl)-3-{4-[2-(tetrahydro-pyran-4-yl)-ethoxy]-naphthalen-1-yl}-urea |

TABLE I-continued

| Structure | Chemical Name |
|---|---|
| 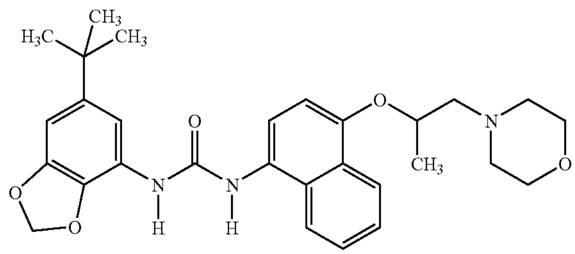 | 1-(6-tert-Butyl-benzo[1,3]dioxol-4-yl)-3-[4-(1-methyl-2-morpholin-4-yl-ethoxy)-naphthalen-1-yl]-urea |
| | 1-(7-Methoxy-1,4,4-trimethyl-1,2,3,4-tetrahydro-quinolin-6-yl)-3-{4-[2-(1-oxo-tetrahydro-$\lambda^4$-thiophen-3-yl)-ethoxy]-naphthalen-1-yl}-urea |
| 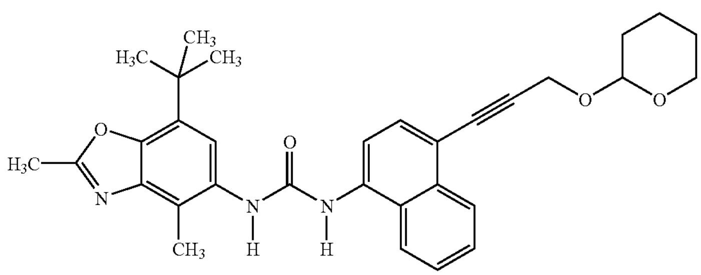 | 1-(7-tert-Butyl-2,4-dimethyl-benzooxazol-5-yl)-3-{4-[3-(tetrahydro-pyran-3-yloxy)-prop-1-ynyl]-naphthalen-1-yl}-urea |
| 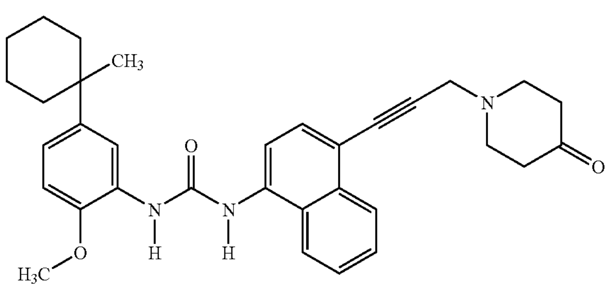 | 1-[2-Methoxy-5-(1-methyl-cyclohexyl)-phenyl]-3-{4-[3-(4-oxo-piperidin-1-yl)-prop-1-ynyl]-naphthalen-1-yl}-urea |
| 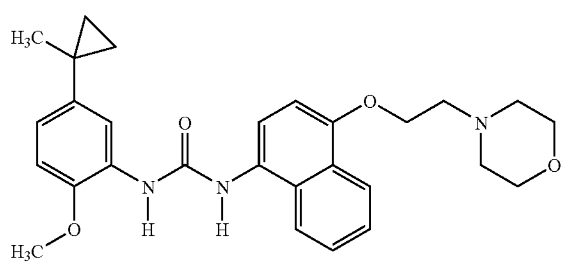 | 1-[2-Methoxy-5-(1-methyl-cyclopropyl)-phenyl]-3-[4-(2-morpholin-4-yl-ethoxy)-naphthalen-1-yl]-urea |

TABLE I-continued

| Structure | Chemical Name |
|---|---|
| 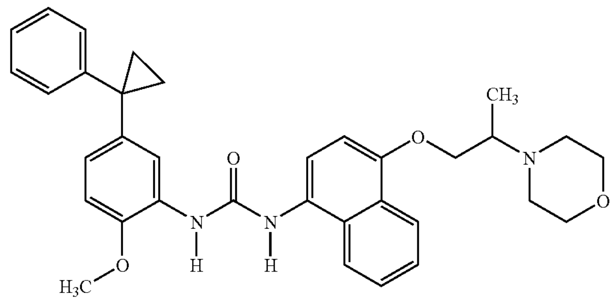 | 1-[2-Methoxy-5-(1-phenyl-cyclopropyl)-phenyl]-3-[4-(2-morpholin-4-yl-propoxy)-naphthalen-1-yl]-urea |
| 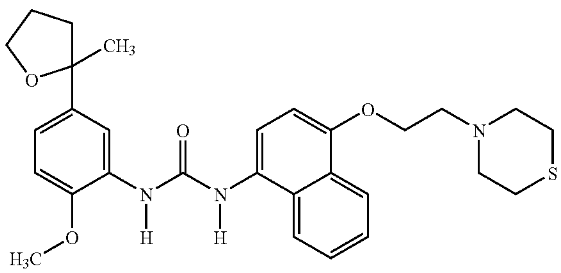 | 1-[2-Methoxy-5-(2-methyl-tetrahydro-furan-2-yl)-phenyl]-3-[4-(2-thiomorpholin-4-yl-ethoxy)-naphthalen-1-yl]-urea |
| 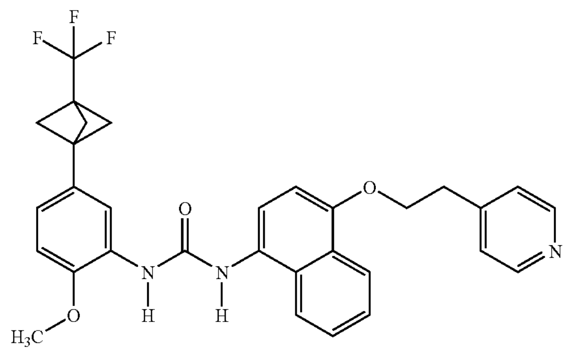 | 1-[2-Methoxy-5-(3-trifluoromethyl-bicyclo[1.1.1]pent-1-yl)-phenyl]-3-[4-(2-pyridin-4-yl-ethoxy)-naphthalen-1-yl]-urea |
| 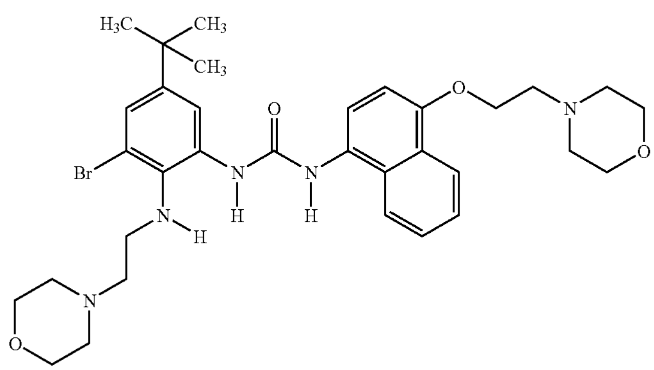 | 1-[3-Bromo-5-tert-butyl-2-(2-morpholin-4-yl-ethylamino)-phenyl]-3-[4-(2-morpholin-4-yl-ethoxy)-naphthalen-1-yl]-urea |
| 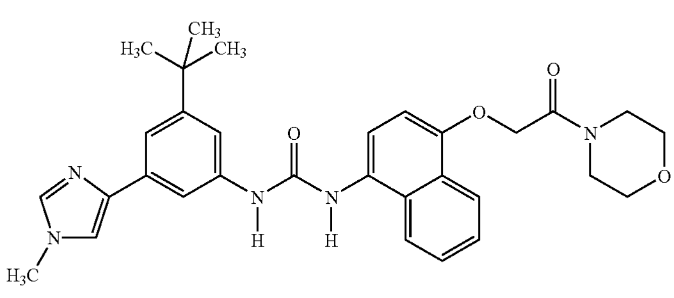 | 1-[3-tert-Butyl-5-(1-methyl-1H-imidazol-4-yl)-phenyl]-3-[4-(2-morpholin-4-yl-2-oxo-ethoxy)-naphthalen-1-yl]-urea |

TABLE I-continued

| Structure | Chemical Name |
|---|---|
| 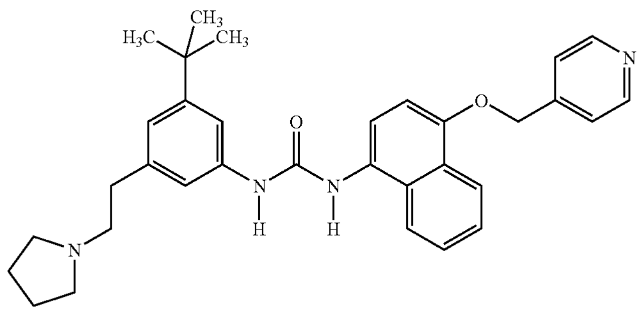 | 1-[3-tert-Butyl-5-(2-pyrrolidin-1-yl-ethyl)-phenyl]-3-[4-(pyridin-4-ylmethoxy)-naphthalen-1-yl]-urea |
| 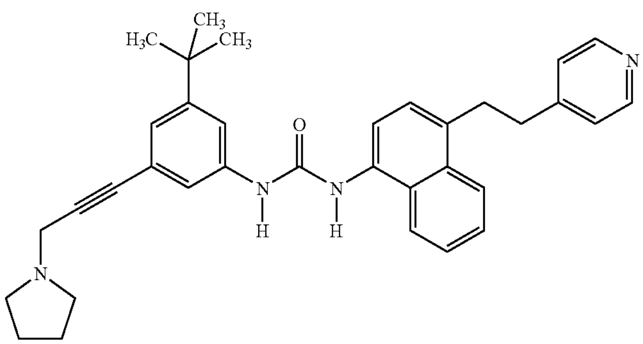 | 1-[3-tert-Butyl-5-(3-pyrrolidin-1-yl-prop-1-ynyl)-phenyl]-3-[4-(2-pyridin-4-yl-ethyl)-naphthalen-1-yl]-urea |
| 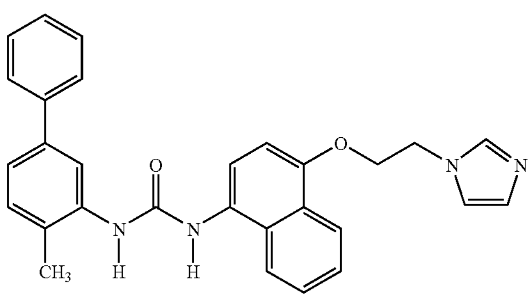 | 1-[4-(2-Imidazol-1-yl-ethoxy)-naphthalen-1-yl]-3-(4-methyl-biphenyl-3-yl)-urea |
| 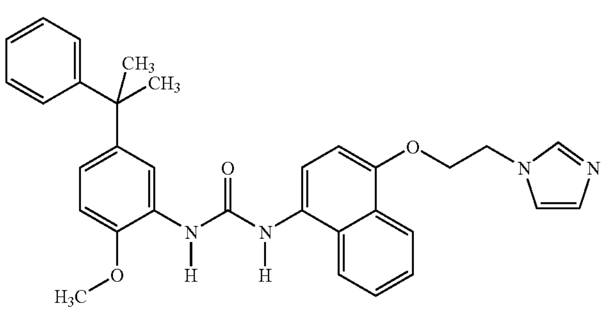 | 1-[4-(2-Imidazol-1-yl-ethoxy)-naphthalen-1-yl]-3-[2-methoxy-5-(1-methyl-1-phenyl-ethyl)-phenyl]-urea |
| 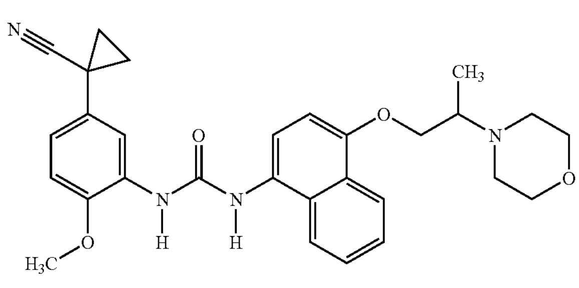 | 1-[5-(1-Cyano-cyclopropyl)-2-methoxy-phenyl]-3-[4-(2-morpholin-4-yl-propoxy)-naphthalen-1-yl]-urea |

TABLE I-continued

| Structure | Chemical Name |
|---|---|
| 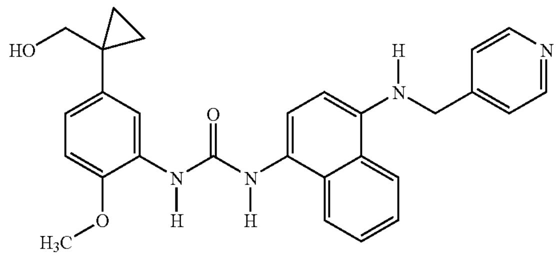 | 1-[5-(1-Hydroxymethyl-cyclopropyl)-2-methoxy-phenyl]-3-{4-[(pyridin-4-ylmethyl)-amino]-naphthalen-1-yl}-urea |
| 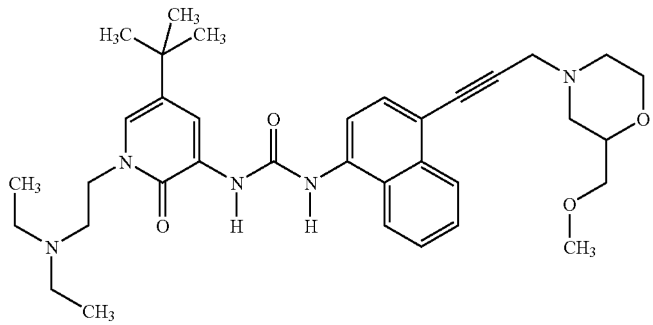 | 1-[5-tert-Butyl-1-(2-diethylamino-ethyl)-2-oxo-1,2-dihydro-pyridin-3-yl]-3-{4-[3-(2-methoxymethyl-morpholin-4-yl)-prop-1-ynyl]-naphthalen-1-yl}-urea |
| 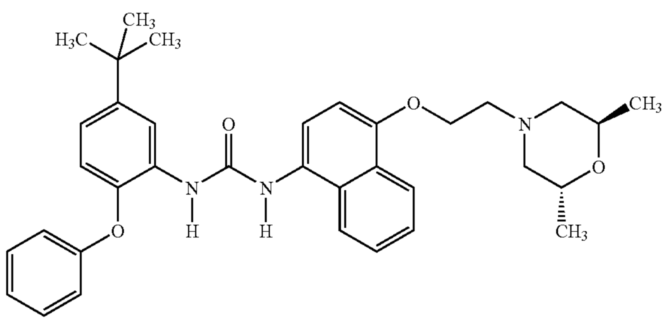 | 1-(5-tert-Butyl--2-phenoxy-phenyl)-3-{4-[2-(2,6-dimethyl-morpholin-4-yl)-ethoxy]-naphthalen-1-yl}-urea |
| 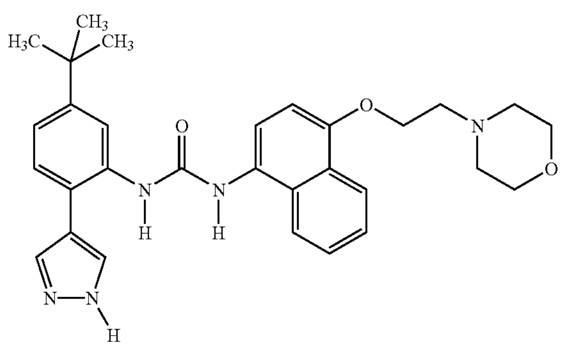 | 1-[5-tert-Butyl-2-(1H-pyrazol-4-yl)-phenyl]-3-[4-(2-morpholin-4-yl-ethoxy)-naphthalen-1-yl]-urea |
| 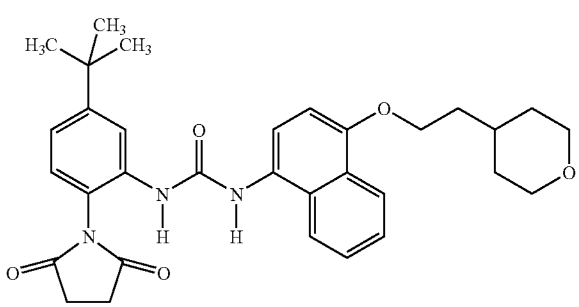 | 1-[5-tert-Butyl-2-(2,5-dioxo-pyrrolidin-1-yl)-phenyl]-3-{4-[2-(tetrahydro-pyran-4-yl)-ethoxy]-naphthalen-1-yl}-urea |

TABLE I-continued

| Structure | Chemical Name |
|---|---|
|  | 1-[5-tert-Butyl-2-(2-methyl-pyrimidin-5-yl)-phenyl]-3-{4-[2-(1-oxo-tetrahydro-λ⁴-thiophen-3-yl)-ethoxy]-naphthalen-1-yl}-urea |
| 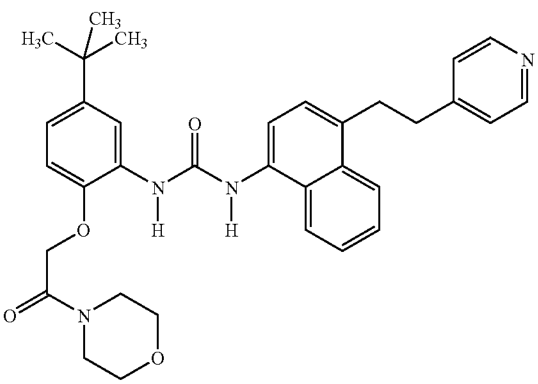 | 1-(5-tert-Butyl-2-methoxy-pyridin-3-yl)-3-{4-[2-(1-oxo-thiomorpholin-4-yl)-ethoxy]-naphthalen-1-yl]-urea |
| 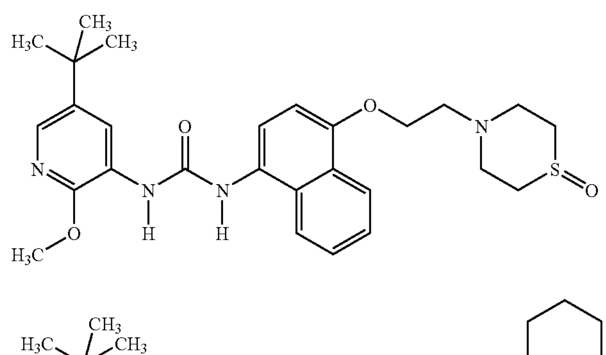 | 1-[5-tert-Butyl-2-(2-morpholin-4-yl-2-oxo-ethoxy)-phenyl]-3-{4-[6-(2-pyridin-4-yl-ethyl)-pyridazin-3-yl]-naphthalen-1-yl}-urea |
| 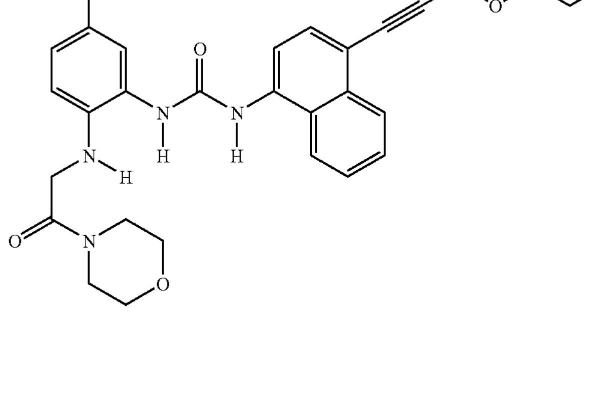 | 1-[5-tert-Butyl-2-(2-morpholin-4-yl-2-oxo-ethyl-amino)-phenyl]-3-{4-[3-(tetrahydro-pyran-3-yloxy)-prop-1-ynyl]-naphthalen-1-yl}-urea |

TABLE I-continued

| Structure | Chemical Name |
|---|---|
| 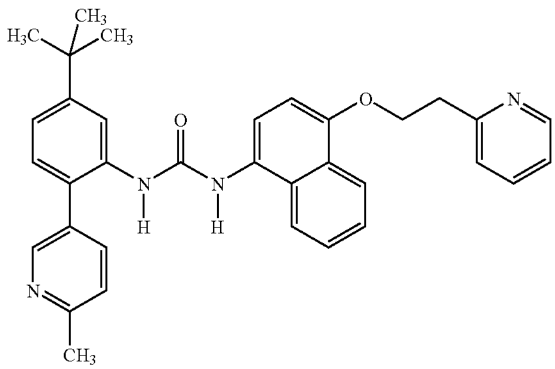 | 1-[5-tert-Butyl-2-(6-methyl-pyridin-3-yl)-phenyl]-3-[4-(2-pyridin-2-yl-ethoxy)-naphthalen-1-yl]-urea |
| 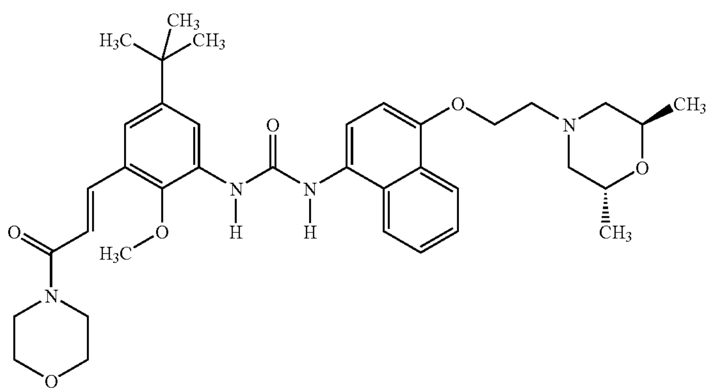 | 1-[5-tert-Butyl-2-methoxy-3-(3-morpholin-4-yl-3-oxo-propenyl)-phenyl]-3-{4-[2-(2,6-dimethyl-morpholin-4-yl)-ethoxy]-naphthalen-1-yl}-urea |
| 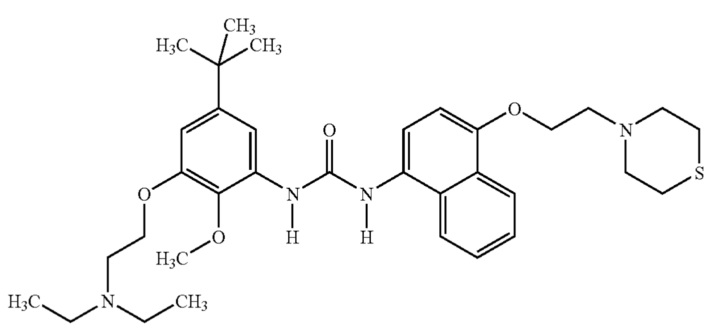 | 1-[5-tert-Butyl-3-(2-diethylamino-ethoxy)-2-methoxy-phenyl]-3-[4-(2-thiomorpholin-4-yl-ethoxy)-naphthalen-1-yl]-urea |
| 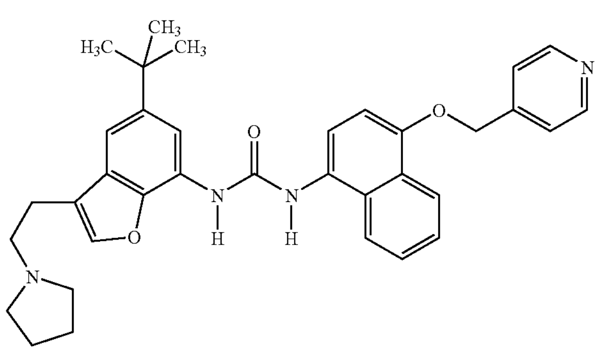 | 1-[5-tert-Butyl-3-(2-pyrrolidin-1-yl-ethyl)-benzofuran-7-yl]-3-[4-(pyridin-4-ylmethoxy)-naphthalen-1-yl]-urea |

TABLE I-continued

| Structure | Chemical Name |
|---|---|
| 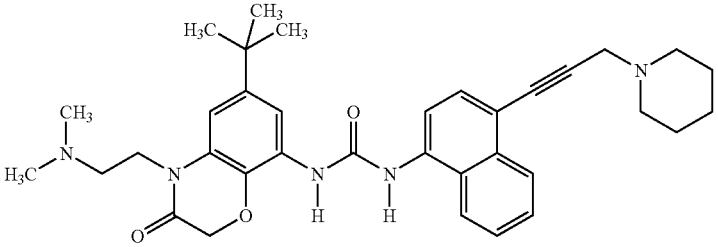 | 1-[6-tert-Butyl-4-(2-dimethylamino-ethyl)-3-oxo-3,4-dihydro-2H-benzo[1,4]oxazin-8-yl]-3-[4-(3-piperidin-1-yl-prop-1-ynyl)-naphthalen-1-yl]-urea |
| 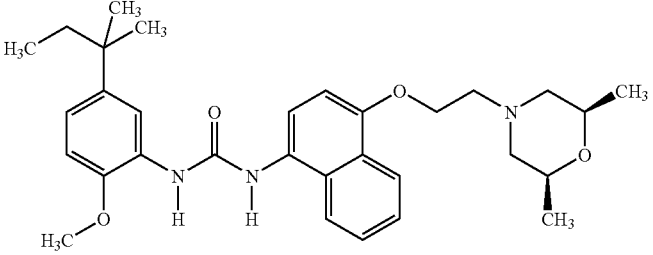 | 1-{4-[2-(2,6-Dimethyl-morpholin-4-yl)-ethoxy]-naphthalen-1-yl}-3-[5-(1,1-dimethyl-propyl)-2-methoxy-phenyl]-urea |
| 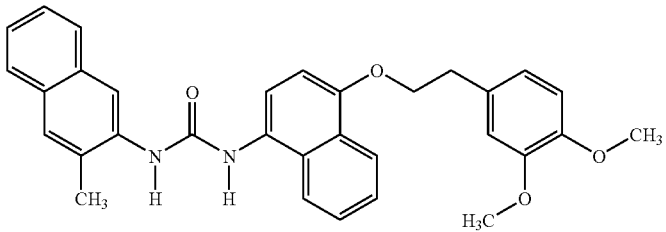 | 1-{4-[2-(3,4-Dimethoxy-phenyl)-ethoxy]-naphthalen-1-yl}-3-(3-methyl-naphthalen-2-yl)-urea |
| 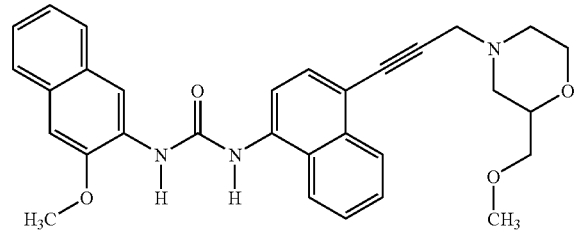 | 1-{4-[3-(2-Methoxymethyl-morpholin-4-yl)-prop-1-ynyl]-naphthalen-1-yl}-3-(3-methoxy-naphthalen-2-yl)-urea |
| 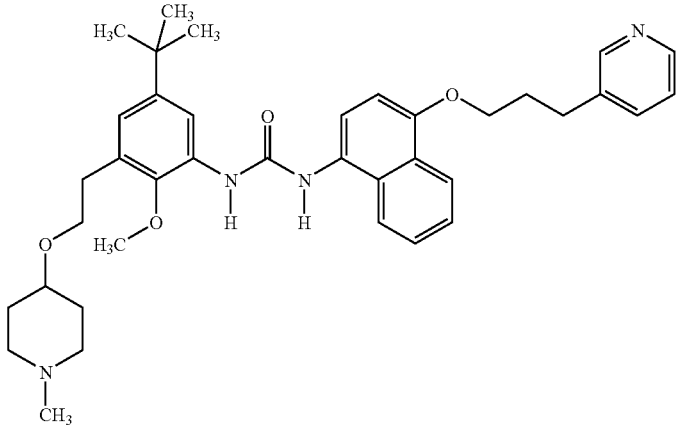 | 1-{5-tert-Butyl-2-methoxy-3-[2-(1-methyl-piperidin-4-yloxy)-ethyl]-phenyl}-3-[4-(3-pyridin-3-yl-propoxy)-naphthalen-1-yl]-urea |

TABLE I-continued

| Structure | Chemical Name |
|---|---|
| 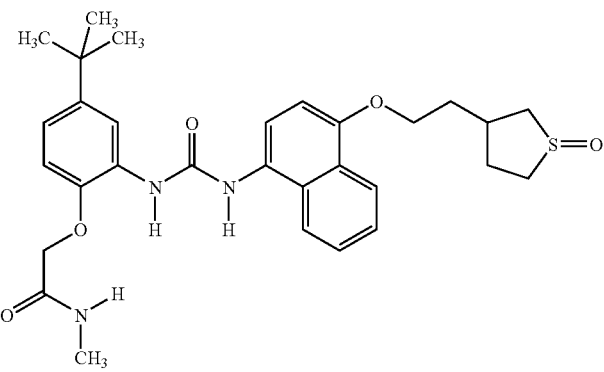 | 2-[4-tert-Butyl-2-(3-{4-[2-(1-oxo-tetrahydro-thiophen-3-yl)-ethoxy]-naphthalen-1-yl}-ureido)-phenoxy]-N-methyl-acetamide |
| 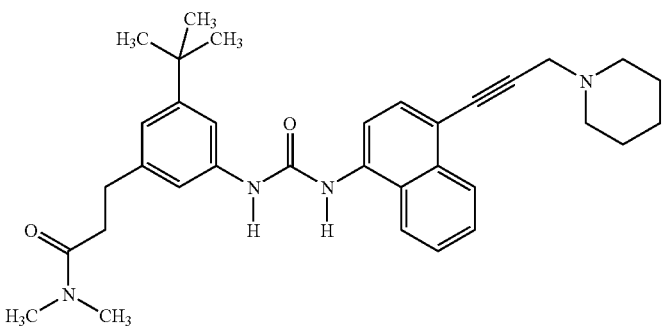 | 3-(3-tert-Butyl-5-{3-[4-(3-piperidin-1-yl-prop-1-ynyl)-naphthalen-1-yl]-ureido}-phenyl)-N,N-dimethyl-propionamide |
| 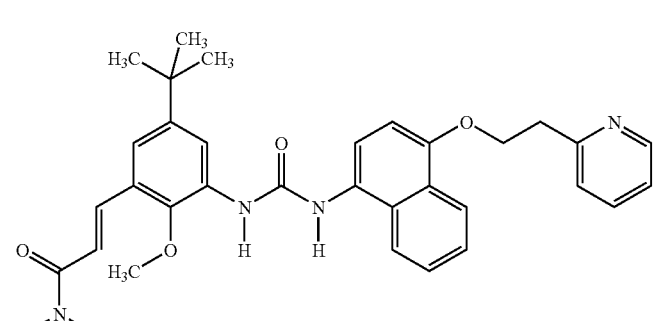 | 3-(5-tert-Butyl-2-methoxy-3-{3-[4-(2-pyridin-2-yl-ethoxy)-naphthalen-1-yl]-ureido}-phenyl)-acrylamide |
| 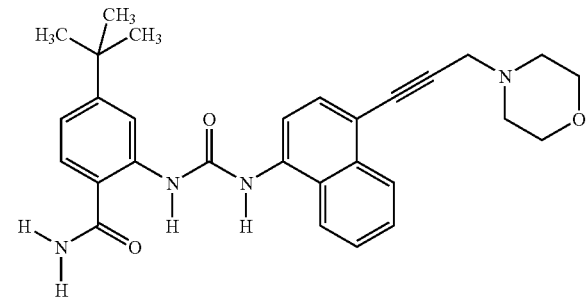 | 4-tert-Butyl-2-{3-[4-(3-morpholin-4-yl-prop-1-ynyl)-naphthalen-1-yl]-ureido}-benzamide |

| Structure | Chemical Name |
|---|---|
| 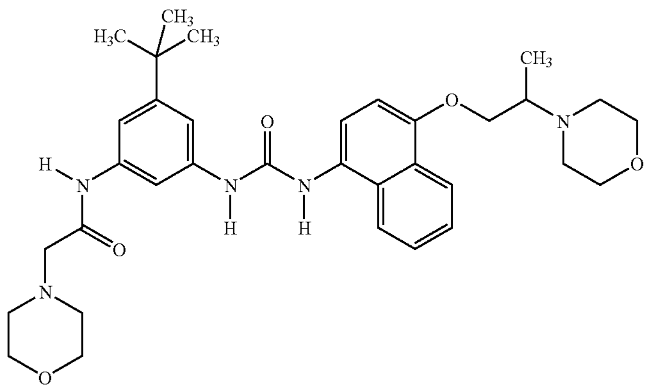 | N-(3-tert-Butyl-5-{3-[4-(2-morpholin-4-yl-propoxy)-naphthalen-1-yl]-ureido}-phenyl)-2-morpholin-4-yl-acetamide |
| 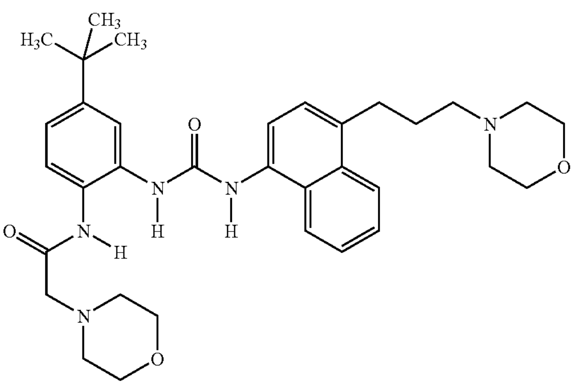 | N-(4-tert-Butyl-2-{3-[4-(3-morpholin-4-yl-propyl)-naphthalen-1-yl]-ureido}-phenyl)-2-morpholin-4-yl-acetamide |
| 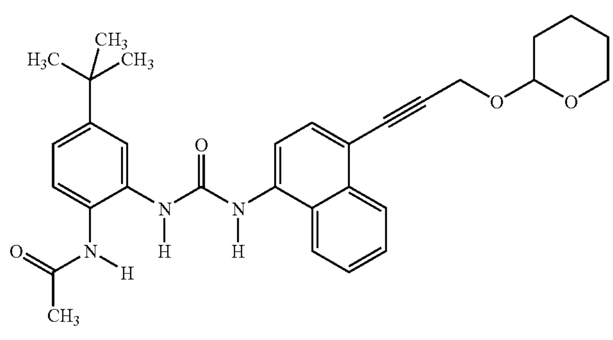 | N-[4-tert-Butyl-2-(3-{4-[3-(tetrahydro-pyran-2-yloxy)-prop-1-ynyl]-naphthalen-1-yl}-ureido)-phenyl]-acetamide |
| 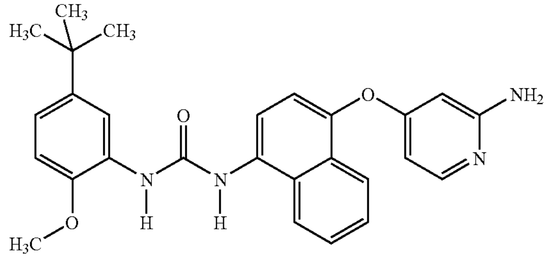 | 1-(5-tert-Butyl-2-methoxyphenyl)-3-[4-(2-aminopyridin-4-yl-oxy)-naphthalen-1-yl]-urea, |

TABLE I-continued

| Structure | Chemical Name |
|---|---|
| 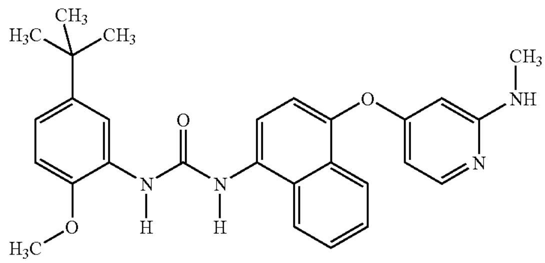 | 1-(5-tert-Butyl-2-methoxyphenyl)-3-[4-(2-(methylamino)pyridin-4-yl-oxy)-naphthalen-1-yl]-urea, |
| 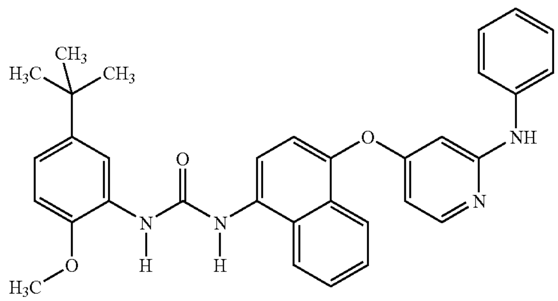 | 1-(5-tert-Butyl-2-methoxyphenyl)-3-[4-(2-(phenylamino)pyridin-4-yl-oxy)-naphthalen-1-yl]-urea, |
| 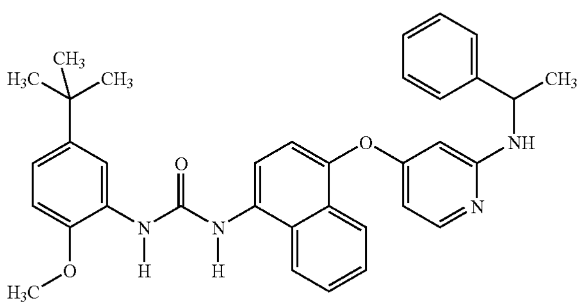 | 1-(5-tert-Butyl-2-methoxyphenyl)-3-[4-(2-(1-phenylethylamino)pyridin-4-yl-oxy)-naphthalen-1-yl]-urea |
| 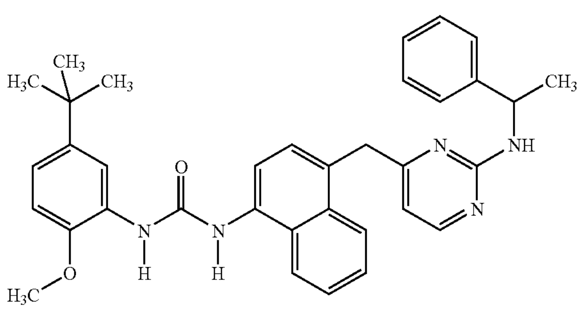 | 1-(5-tert-Butyl-2-methoxyphenyl)-3-[4-(2-(1-phenylethylamino)pyrimid-4-yl-methyl)-naphthalen-1-yl]-urea |
| 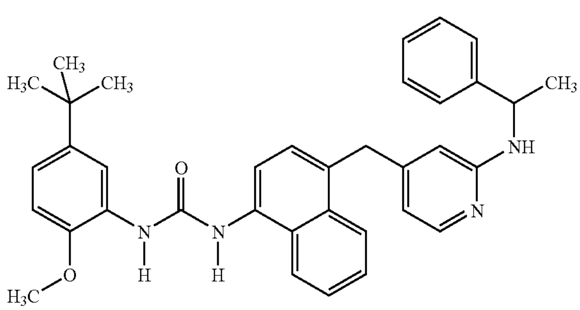 | 1-(5-tert-Butyl-2-methoxyphenyl)-3-[4-(2-(1-phenylethylamino)pyridin-4-yl-methyl)-naphthalen-1-yl]-urea |

TABLE I-continued

| Structure | Chemical Name |
|---|---|
| 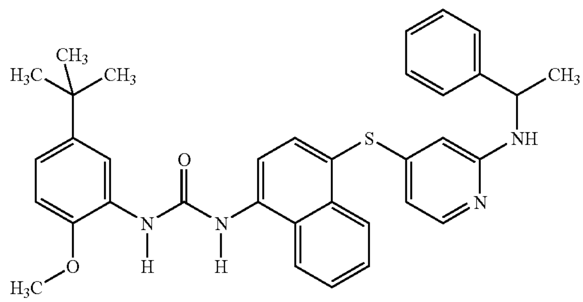 | 1-(5-tert-Butyl-2-methoxyphenyl)-3-[4-(2-(1-phenylethylamino)pyridin-4-yl-thio)-naphthalen-1-yl]-urea |
| 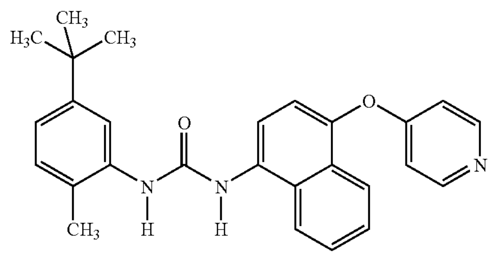 | 1-[5-tert-butyl-2-methylphenyl]-3-[4-(4-pyridinyloxy)-naphthalen-1-yl]-urea |
| 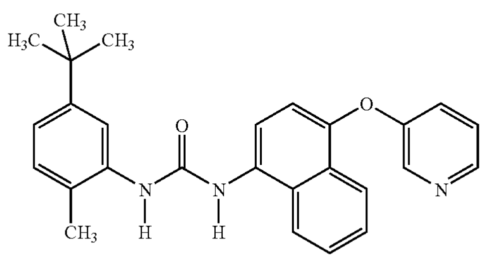 | 1-[5-tert-butyl-2-methylphenyl]-3-[4-(3-pyridinyloxy)-naphthalen-1-yl]-urea |
| 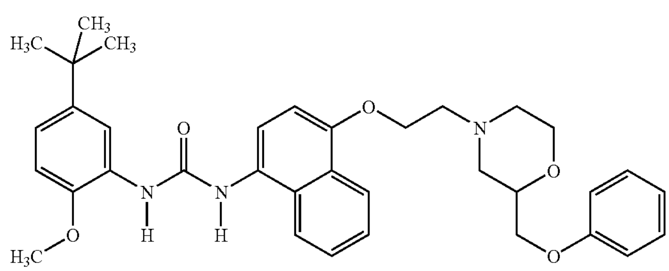 | 1-[5-tert-butyl-2-methoxyphenyl]-3-[4-(2-(2-phenoxymethyl)morpholin-4-yl-ethoxy)-naphthalen-1-yl]-urea |
| 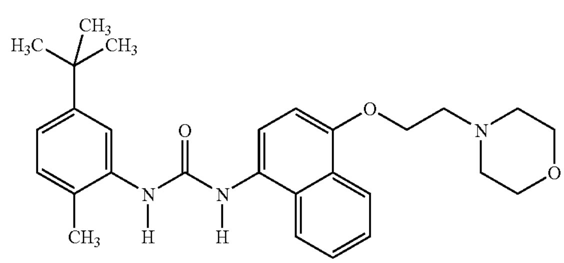 | 1-[5-tert-butyl-2-methylphenyl]-3-[4-(2-morpholin-4-yl-ethoxy)-naphthalen-1-yl]-urea |

TABLE I-continued

| Structure | Chemical Name |
|---|---|
| 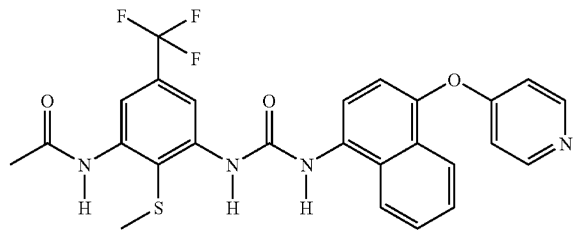 | 1-[3-acetamido-5-trifluoromethyl-2-methylthiophenyl]-3-[4-(3-pyridinyloxy)-naphthalen-1-yl]-urea |
| 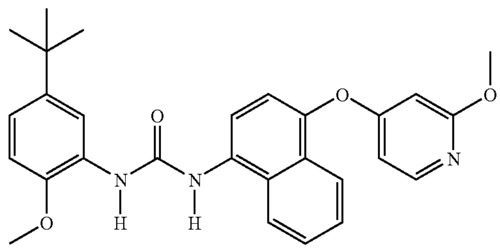 | 1-(5-tert-Butyl-2-methoxyphenyl)-3-[4-(2-methoxy-pyridin-4-yl-oxy)-naphthalen-1-yl]-urea |
| 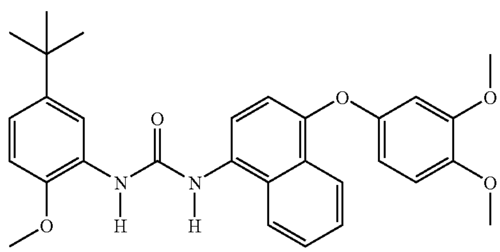 | 1-(5-tert-Butyl-2-methoxyphenyl)-3-[4-(3,4-dimethoxyphenyl-oxy)-naphthalen-1-yl]-urea |
| 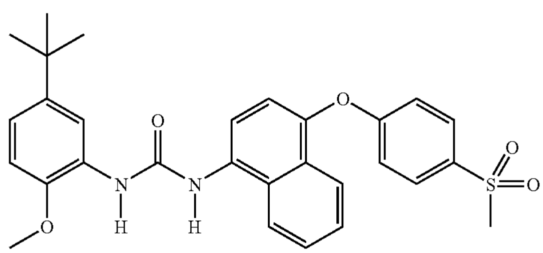 | 1-(5-tert-Butyl-2-methoxyphenyl)-3-[4-(4-methylsulfonyl-oxy)-naphthalen-1-yl]-urea |
| 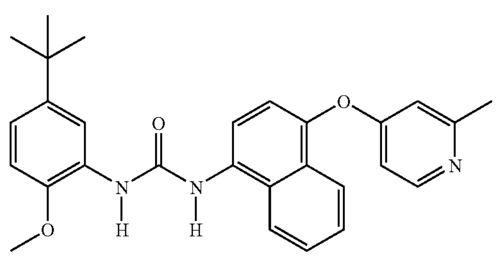 | 1-(5-tert-Butyl-2-methoxyphenyl)-3-[4-(2-methyl-pyridin-4-yl-oxy)-naphthalen-1-yl]-urea |
| 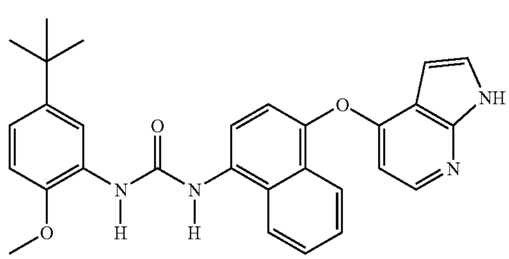 | 1-(5-tert-Butyl-2-methoxyphenyl)-3-[4-(1H-pyrolo[2,3-b]pyridin-4-yl-oxy)-naphthalen-1-yl]-urea |

TABLE I-continued

| Structure | Chemical Name |
|---|---|
| 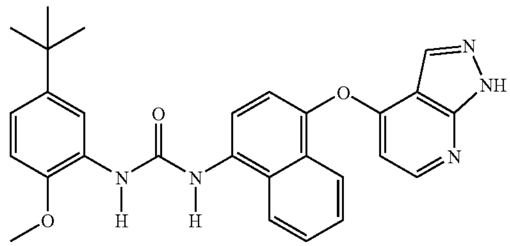 | 1-(5-tert-Butyl-2-methoxyphenyl)-3-[4-(1H-pyrazolo[2,3-b]pyridin-4-yl-oxy)-naphthalen-1-yl]-urea |
| 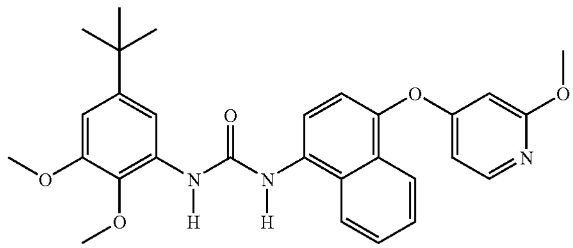 | 1-(5-tert-Butyl-2,3-dimethoxyphenyl)-3-[4-(2-methoxy-pyridin-4-yl-oxy)-naphthalen-1-yl]-urea |
| 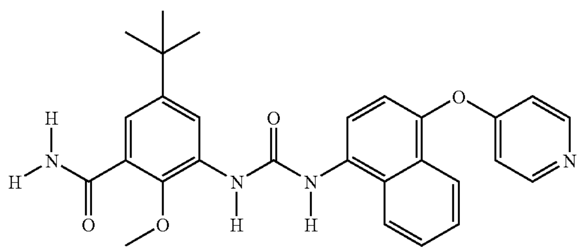 | 5-tert-Butyl-2-methoxy-3-{3-[-(pyridin-4-yl-oxy)naphthalen-1-yl]ureido}benzamide |
| 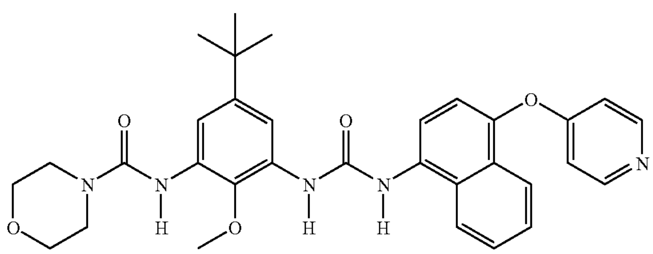 | Morpholine-4-carboxylic acid(5-tert-butyl-2-methoxy-3-{3-[-(pyridin-4-yl-oxy)naphthalen-1-yl]ureido}phenyl)amide |
| 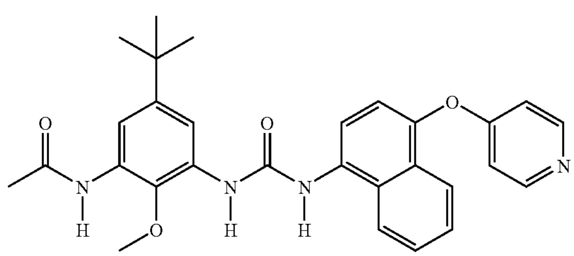 | N-(5-tert-Butyl-2-methoxy-3-{3-[-(pyridin-4-yl-oxy)naphthalen-1-yl]ureido}phenyl)acetamide |
| 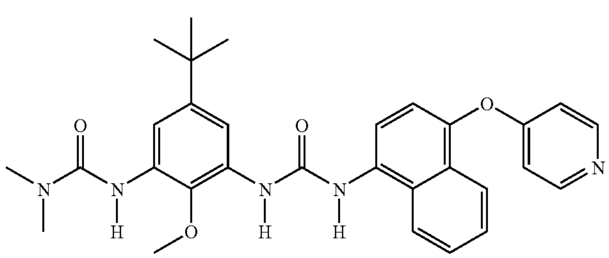 | 3-(5-tert-Butyl-2-methoxy-3-{3-[-(pyridin-4-yl-oxy)naphthalen-1-yl]ureido}phenyl)-1,1-dimethylurea |

TABLE I-continued

| Structure | Chemical Name |
|---|---|
| 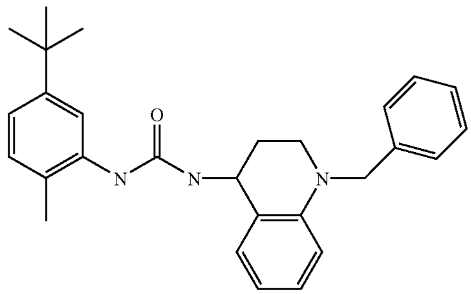 | 1-(1-Benzyl-1,2,3,4-tetrahydro-quinolin-4-yl)-3-(5-tert-butyl-2-methyl-phenyl)-urea |
| 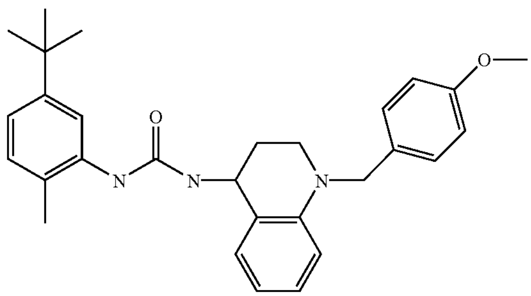 | 1-(5-tert-Butyl-2-methyl-phenyl)-3-[1-(4-methoxy-benzyl)-1,2,3,4-tetrahydro-quinolin-4-yl]-urea |
| 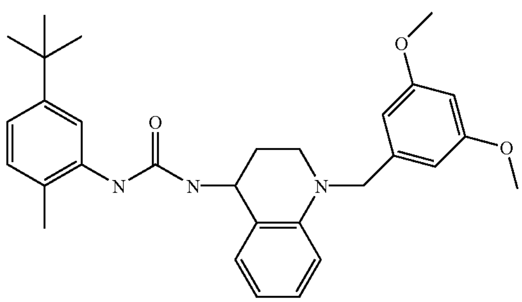 | 1-(5-tert-Butyl-2-methyl-phenyl)-3-[1-(3,5-dimethoxy-benzyl)-1,2,3,4-tetrahydro-quinolin-4-yl]-urea |
| 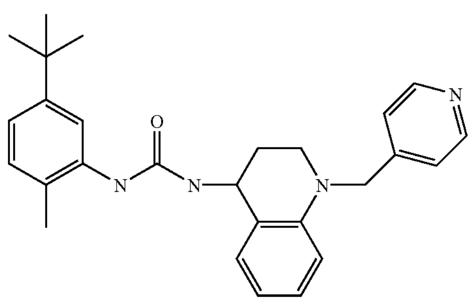 | 1-(5-tert-Butyl-2-methyl-phenyl)-3-(1-pyridin-4-ylmethyl-1,2,3,4-tetrahydro-quinolin-4-yl)-urea |
| 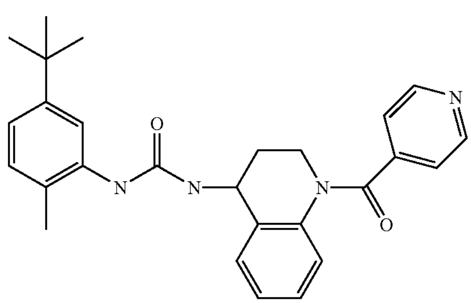 | 1-(5-tert-Butyl-2-methyl-phenyl)-3-[1-(pyridine-4-carbonyl)-1,2,3,4-tetrahydro-quinolin-4-yl]-urea |

TABLE I-continued

| Structure | Chemical Name |
|---|---|
| 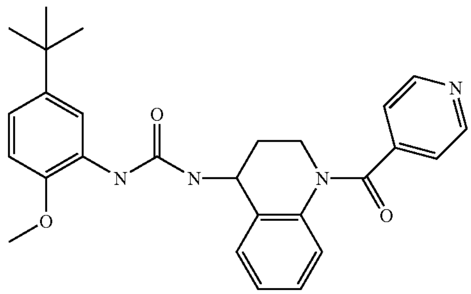 | 1-(5-tert-Butyl-2-methoxy-phenyl)-3-[1-(pyridine-4-carbonyl)-1,2,3,4-tetrahydro-quinolin-4-yl]-urea |
| 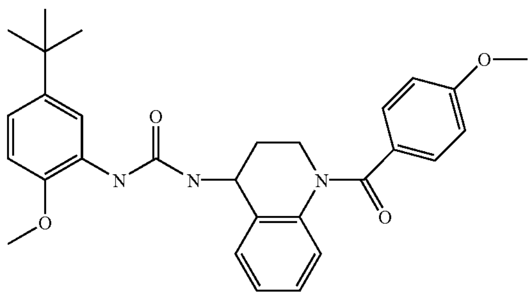 | 1-(5-tert-Butyl-2-methoxy-phenyl)-3-[1-(4-methoxy-benzoyl)-1,2,3,4-tetrahydro-quinolin-4-yl]-urea |
| 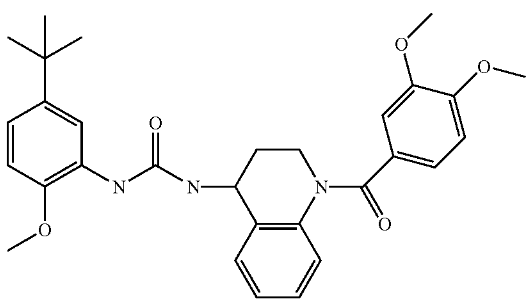 | 1-(5-tert-Butyl-2-methoxy-phenyl)-3-[1-(3,4-dimethoxy-benzoyl)-1,2,3,4-tetrahydro-quinolin-4-yl]-urea |
| 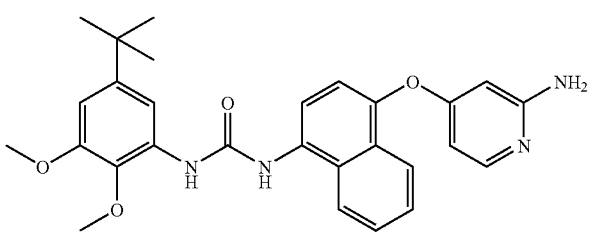 | 1-[4-(2-Amino-pyridin-4-yloxy)-naphthalen-1-yl]-3-(5-tert-butyl-2,3-dimethoxy-phenyl)-urea |
| 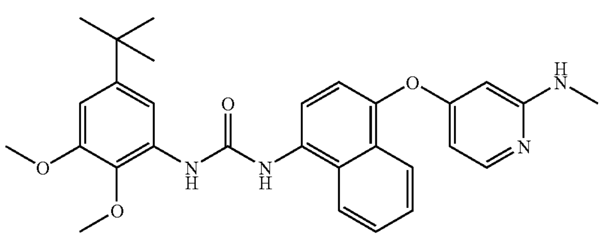 | 1-(5-tert-Butyl-2,3-dimethoxy-phenyl)-3-[4-(2-methylamino-pyridin-4-yloxy)-naphthalen-1-yl]-urea |

TABLE I-continued

| Structure | Chemical Name |
|---|---|
| 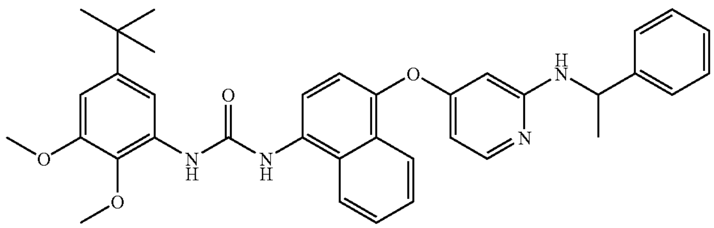 | 1-(5-tert-Butyl-2,3-dimethoxy-phenyl)-3-{4-[2-(1-phenyl-ethylamino)-pyridin-4-yloxy]-naphthalen-1-yl}-urea |
| 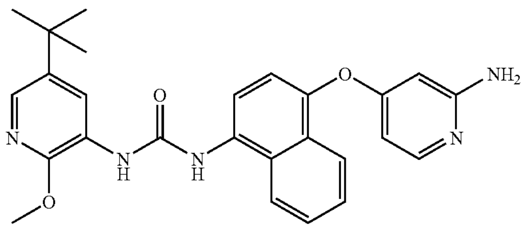 | 1-[4-(2-Amino-pyridin-4-yloxy)-naphthalen-1-yl]-3-(5-tert-butyl-2-methoxy-pyridin-3-yl)-urea |
| 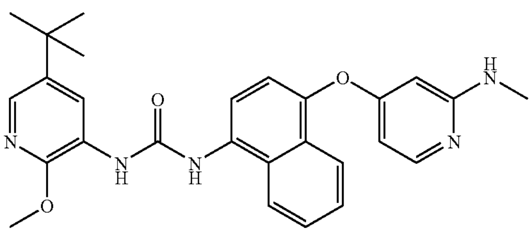 | 1-(5-tert-Butyl-2-methoxy-pyridin-3-yl)-3-[4-(2-methylamino-pyridin-4-yloxy)-naphthalen-1-yl]-urea |
| 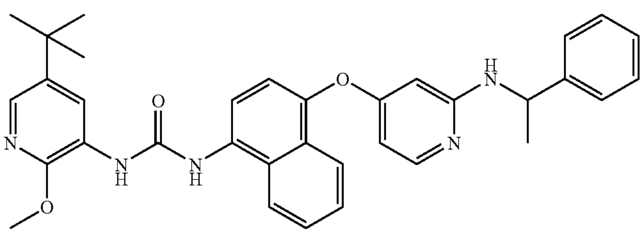 | 1-(5-tert-Butyl-2-methoxy-pyridin-3-yl)-3-{4-[2-(1-phenyl-ethylamino)-pyridin-4-yloxy]-naphthalen-1-yl}-urea |
| 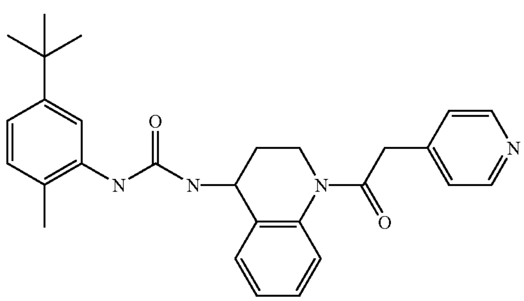 | 1-(5-tert-Butyl-2-methylphenyl)-3-[1-(2-pyridin-4-yl-acetyl)-1,2,3,4-tetrahydroquinolin-4-yl]-urea |
| | 1-(5-tert-Butyl-2-methoxyphenyl)-3-[1-(2-pyridin-4-yl-acetyl)-1,2,3,4-tetrahydroquinolin-4-yl]-urea | and the pharmaceutically acceptable salts thereof.

TABLE I-continued

| Structure | Chemical Name |
|---|---|
| Preferred compounds are selected from: | |
| 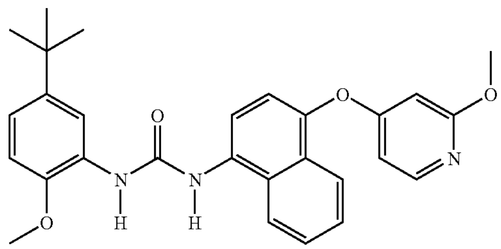 | 1-(5-tert-Butyl-2-methoxyphenyl)-3-[4-(2-methoxy-pyridin-4-yl-oxy)-naphthalen-1-yl]-urea |
| 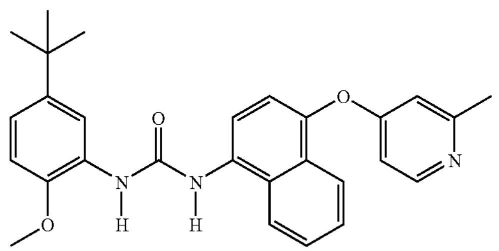 | 1-(5-tert-Butyl-2-methoxyphenyl)-3-[4-(2-methyl-pyridin-4-yl-oxy)-naphthalen-1-yl]-urea |
| 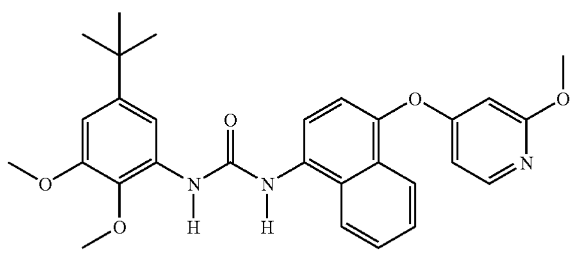 | 1-(5-tert-Butyl-2,3-dimethoxyphenyl)-3-[4-(2-methoxy-pyridin-4-yl-oxy)-naphthalen-1-yl]-urea |
| 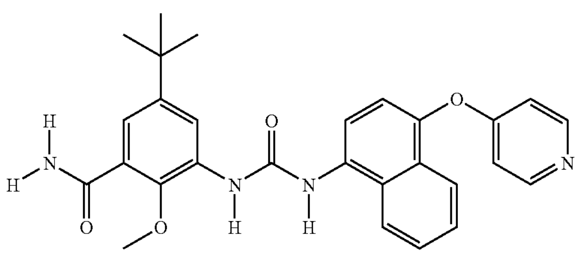 | 5-tert-Butyl-2-methoxy-3-{3-[-(pyridin-4-yl-oxy)naphthalen-1-yl]ureido}benzamide |
| 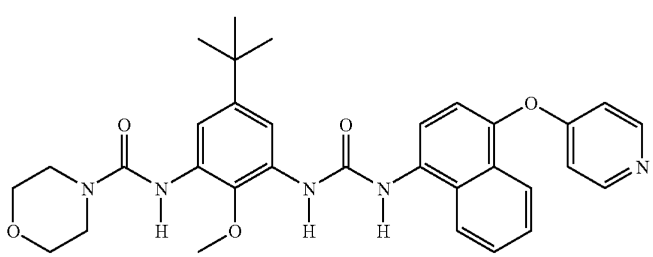 | Morpholine-4-carboxylic acid(5-tert-butyl-2-methoxy-3-{3-[-(pyridin-4-yl-oxy)naphthalen-1-yl]ureido}phenyl)amide |
| 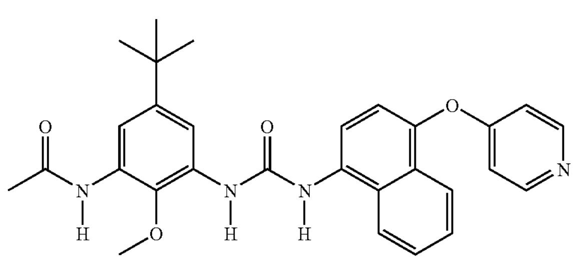 | N-(5-tert-Butyl-2-methoxy-3-{3-[-(pyridin-4-yl-oxy)naphthalen-1-yl]ureido}phenyl)acetamide |

TABLE I-continued

| Structure | Chemical Name |
|---|---|
| 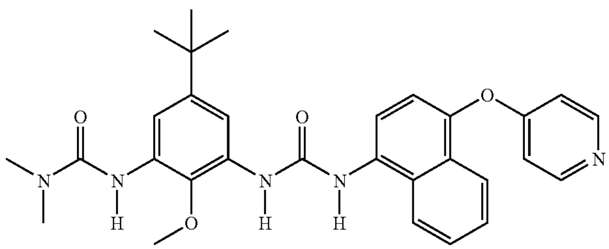 | 3-(5-tert-Butyl-2-methoxy-3-{3-[-(pyridin-4-yl-oxy)naphthalen-1-yl]ureido}phenyl)-1,1-dimethylurea |
| 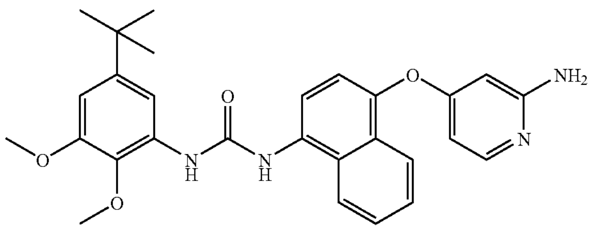 | 1-[4-(2-Amino-pyridin-4-yloxy)-naphthalen-1-yl]-3-(5-tert-butyl-2,3-dimethoxy-phenyl)-urea |
| 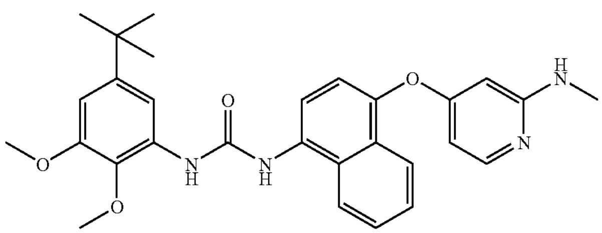 | 1-(5-tert-Butyl-2,3-dimethoxy-phenyl)-3-[4-(2-methylamino-pyridin-4-yloxy)-naphthalen-1-yl]-urea |
| 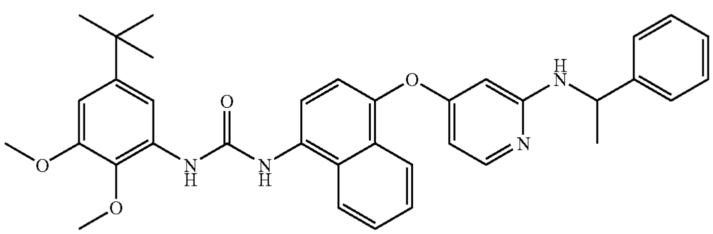 | 1-(5-tert-Butyl-2,3-dimethoxy-phenyl)-3-{4-[2-(1-phenyl-ethylamino)-pyridin-4-yloxy]-naphthalen-1-yl}-urea |
| 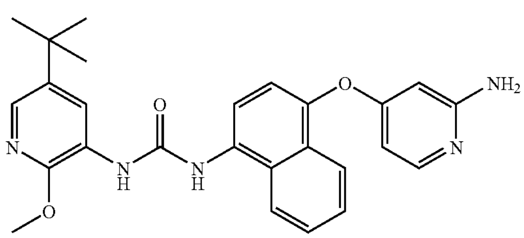 | 1-[4-(2-Amino-pyridin-4-yloxy)-naphthalen-1-yl]-3-(5-tert-butyl-2-methoxy-pyridin-3-yl)-urea |
| 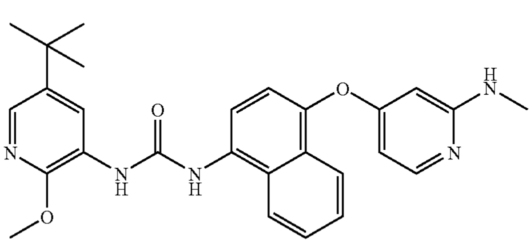 | 1-(5-tert-Butyl-2-methoxy-pyridin-3-yl)-3-[4-(2-methylamino-pyridin-4-yloxy)-naphthalen-1-yl]-urea |

TABLE I-continued

| Structure | Chemical Name |
|---|---|
| (structure shown) | 1-(5-tert-Butyl-2-methoxy-pyridin-3-yl)-3-{4-[2-(1-phenyl-ethylamino)-pyridin-4-yloxy]-naphthalen-1-yl}-urea | and the pharmaceutically acceptable salts thereof.

The following compounds found in Table I were evaluated, all had IC$_{50}$<10 uM in the "Inhibition of TNF Production in THP Cells" assay described below:

1-(5-tert-Butyl-2-methylphenyl)-3-[4-(2-aminopyridin-4-yl-oxy)naphthalen-1-yl]urea;

1-(5-tert-Butyl-2-morpholin-4-yl-phenyl)-3-[4-(2-morpholin-4-yl-ethoxy)-naphthalen-1-yl]-urea;

1-[3-Bromo-5-tert-butyl-2-(2-morpholin-4-yl-ethylamino)-phenyl]-3-[4-(2-morpholin-4-yl-ethoxy)-naphthalen-1-yl]-urea;

1-[5-tert-butyl-2-methylphenyl]-3-[4-(4-pyridinyloxy)-naphthalen-1-yl]-urea;

1-[5-tert-butyl-2-methylphenyl]-3-[4-(3-pyridinyloxy)-naphthalen-1-yl]-urea;

1-[5-tert-butyl-2-methoxyphenyl]-3-[4-(2-(2-phenoxymethyl)morpholin-4-yl-ethoxy)-naphthalen-1-yl]-urea and 1-[5-tert-butyl-2-methylphenyl]-3-[4-(2-morpholin-4-yl-ethoxy)-naphthalen-1-yl]-urea.

ASSESSMENT OF BIOLOGICAL PROPERTIES

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells (2×10$^6$ cells/mL, final conc.; American Type Culture Company, Rockville, Md.) were added to 96 well polypropylene round bottomed culture plates (Costar 3790; sterile) containing 125 µL test compound (2 fold concentrated) or DMSO vehicle (controls, blanks). DMSO concentration did not exceed 0.2% final. Cell mixture was allowed to preincubate for 30 min, 37° C., 5% CO$_2$ prior to stimulation with lipopolysaccharide (LPS; 1 µg/mL final; Siga L-2630, from *E.coli* serotype 0111.B4; stored as 1 mg/mL stock in endotoxin screened distilled H$_2$O at −80° C.). Blanks (unstimulated) received H$_2$O vehicle; final incubation volume was 250 µl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC$_{50}$ value is the concentration of the test compound that caused a 50% decrease in the maximal TNFα production.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1β, GM-CSF, IL-6 and IL-8 can be demonstrated (for example, see J. C. Lee et al., 1988, *Int. J. Immunopharmacol.*, 10, 835).

What is claimed is:

1. A Compound of the formula (I):

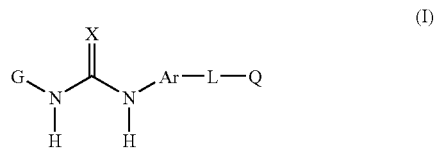

wherein:
G is:
  pyridinyl substituted by one or more R$_1$, R$_2$ or R$_3$;
Ar is:
  naphthyl, tetrahydronaphthyl, indanyl, or indenyl each optionally substituted by one or more R$_4$ or R$_5$ groups;
L is a:
  O, NH, CH$_2$ or S(O)$_m$, O—CH$_2$—, O—CH$_2$CH$_2$, O—CH$_2$CH$_2$CH$_2$, O—CH$_2$CH$_2$(CH$_3$), O—CH$_2$(CH$_3$)CH$_2$, NHCH$_2$, NHCH$_2$CH$_2$, NHCH$_2$CH$_2$CH$_2$, S(O)$_m$CH$_2$, S(O)$_m$CH$_2$CH$_2$, S(O)$_m$CH$_2$CH$_2$CH$_2$, CH$_2$CH$_2$, CH$_2$CH$_2$CH$_2$, O—CH$_2$C(O), HC≡C—CH$_2$ or HC≡C—CH$_2$O
Q is:
  pyridinyl, pyrimidinyl, pyridazinyl, imidazolyl, benzimidazolyl, furanyl, thienyl, pyranyl, naphthyridinyl, pyrazinyl, pyrazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl, which are optionally substituted with one to three C$_{1-6}$ alkyl, $C_{1-6}$ alkoxy, hydroxy, amino, mono- or di-($C_{1-3}$ alkyl)amino, mono- or di-(phenyl-$C_{1-3}$ alkyl)amino, $C_{1-6}$ alkyl-S(O)$_m$, phenyl-$C_{1-3}$-alkoxy or phenylamino wherein the phenyl ring is optionally substituted with one to two halogen, $C_{1-6}$ alkyl or $C_{1-6}$ alkoxy;

tetrahydropyranyl, tetrahydrofuranyl, 1,3-dioxolanone, 1,3-dioxanone, 1,4-dioxanyl, morpholino, thiomorpholino, thiomorpholino sulfoxide, thiomorpholino sulfone, piperazinyl, piperidinyl, piperidinonyl, tetrahydropyrimidonyl, pentamethylene sulfide, pentamethylene sulfoxide, pentamethylene sulfone, tetramethylene sulfide, tetramethylene sulfoxide or tetramethylene sulfone which are optionally substituted with one to three $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl or $C_{1-3}$ alkoxy-$C_{1-3}$ alkyl;

each $R_1$ is independently:

$C_{3-10}$ branched or unbranched alkyl optionally partially or fully halogenated, and optionally substituted with one to three $C_{3-10}$ cycloalkyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl each optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and NH$_2$C(O) or mono- or di($C_{1-3}$)alkylaminocarbonyl;

cyclopropyl, cyclobutyl, cyclopentanyl, cyclohexanyl, cycloheptanyl, bicyclopentanyl, bicyclohexanyl or bicycloheptanyl, which are optionally partially or fully halogenated and optionally substituted with one to three $C_{1-3}$ alkyl groups optionally partially or fully halogenated, cyano, hydroxy$C_{1-3}$alkyl or aryl; or an analog of cyclopropyl, cyclobutyl, cyclopentanyl, cyclohexanyl, cycloheptanyl, bicyclopentanyl, bicyclohexanyl or bicycloheptanyl wherein one to three ring methylene groups are replaced independently by O, S(O)$_m$, CHOH, >C=O, >C=S or NH;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each optionally substituted with 1 to 5 halogen, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclohexanyl or bicycloheptanyl, hydroxy, cyano, $C_{1-3}$ alkoxy optionally partially or fully halogenated, NH$_2$C(O) or mono- or di($C_{1-3}$)alkylaminocarbonyl; the $C_{3-10}$ branched or unbranched alkenyl is optionally interrupted by one or more O, N or S(O)$_m$;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

cyano, halogen;

methoxycarbonyl, ethoxycarbonyl or propoxycarbonyl;

silyl containing three $C_{1-4}$ independently branched or unbranched alkyl groups optionally partially or fully halogenated;

$C_{2-6}$ branched or unbranched alkyl-C(O), $C_{2-6}$ branched or unbranched-S, $C_{2-6}$ branched or unbranched-S(O), $C_{2-6}$ branched or unbranched-S(O)$_2$;

$C_{2-6}$ alkynyl branched or unbranched carbon chain optionally partially or fully halogenated, wherein one or more methylene groups are optionally replaced by O, NH and S(O)$_m$ and wherein said alkynyl group is optionally independently substituted with 0-2 oxo groups, pyrroldinyl, pyrrolyl, one or more $C_{1-4}$ branched or unbranched alkyl optionally substituted by one or more halogen atoms, nitrile, morpholino, piperidinyl, piperazinyl, imidazolyl, phenyl, pyridinyl, tetrazolyl, or $C_{1-4}$ branched or unbranched alkylamino optionally substituted by one or more halogen atoms;

each $R_2$, $R_4$, and $R_5$ is independently a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;

$C_{1-6}$ alkoxy, hydroxy, amino, or mono- or di-($C_{1-4}$ alkyl)amino, cyano, halogen;

OR$_6$;

nitro; or mono- or di-($C_{1-4}$ alkyl)amino-S(O)$_2$ optionally partially or fully halogenated, or H$_2$NSO$_2$;

each $R_3$ is independently:

hydrogen, phenyl, naphthyl, pyridinyl, pyrimidinyl, pyrazinyl, pyridazinyl, pyrrolyl, pyrrolidinyl, imidazolyl, pyrazolyl, thienyl, furyl, tetrahydrofuryl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl each optionally substituted with one to five phenyl, naphthyl, heterocycle or heteroaryl wherein the heterocyclic and heteraryl moiety is as hereinabove described in this paragraph, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, cyano, $C_{1-3}$ alkoxy optionally partially or fully halogenated, phenyloxy, naphthyloxy, heteraryloxy wherein the heterocyclic moiety is as hereinabove described in this paragraph, nitro, amino, mono- or di-($C_{1-3}$)alkylamino, phenylamino, naphthylamino, heterocyclic or heteroaryl amino wherein the heterocyclic or heteroaryl moiety is as hereinabove described in this paragraph, NH$_2$C(O), a mono- or di-($C_{1-3}$)alkyl aminocarbonyl, $C_{1-5}$ alkyl-C(O)— $C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$)alkylamino-S(O)$_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy-mono- or di-($C_{1-5}$)-alkyl-amino;

a fused aryl selected from benzocyclobutanyl, indanyl, indenyl, dihydronaphthyl, tetrahydronaphthyl, benzocycloheptanyl and benzocycloheptenyl, or a fused heterocycle selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclic ring is optionally independently substituted with 1 to 3 groups selected from phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ branched or unbranched alkyl optionally partially or fully halogenated, halo, cyano, $C_{1-3}$ alkoxy optionally partially or fully halogenated, phenyloxy, naphthyloxy, heterocyclicoxy heteroaryloxy wherein the heterocyclic or heteroaryl moiety is as hereinabove described in this paragraph, nitro, amino, mono- or di-$(C_{1-3})$ alkylamino, phenylamino, naphthylamino, heterocyclicamino or heteroarylamino wherein the heterocyclic or heteroaryl moiety is as hereinabove described in this paragraph, $NH_2C(O)$, a mono- or di-$(C_{1-3})$ alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-$(C_{1-3})$alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl and $R_{15}$—$C_{1-5}$ alkyl$(R_{16})$N;

cyclopropyl, cyclobutyl, cyclopentanyl, cyclohexanyl, cycloheptanyl, bicyclopentanyl, bicyclohexanyl or bicycloheptanyl optionally partially or fully halogenated and optionally substituted with one to three $C_{1-3}$ alkyl groups, or an analog of cyclopropyl, cyclobutyl, cyclopentanyl, cyclohexanyl, cycloheptanyl, bicyclopentanyl, bicyclohexanyl or bicycloheptanyl wherein one to three ring methylene groups are replaced independently by O, $S(O)_m$, CHOH, >C═O, >C═S or NH;

cyclopentenyl, cyclohexenyl, cyclohexadienyl, cycloheptenyl, cycloheptadienyl, bicyclohexenyl or bicycloheptenyl each optionally substituted with one to three $C_{1-3}$ alkyl groups;

$C_{1-4}$ branched or unbranched alkyl-phenyl-C(O)—$C_{1-4}$ branched or unbranched alkyl, $C_{1-4}$ branched or unbranched alkyl-C(O)—$C_{1-4}$ branched or unbranched alkyl, $C_{1-4}$ branched or unbranched alkyl-phenyl-$S(O)_m$—$C_{1-4}$ branched or unbranched alkyl;

$C_{1-6}$ branched or unbranched alkyl or $C_{1-6}$ branched or unbranched alkoxy each is optionally partially or fully halogenated or optionally substituted with $R_{17}$;

$C_{1-6}$ branched or unbranched alkyl optionally substituted with $OR_{18}$;

amino or $C_1$-$C_5$ branched or unbranched mono- or di-alkylamino optionally substituted with $R_{19}$;

cyclopropyloxy, cyclobutyloxy, cyclopentyloxy, cyclohexyloxy or cycloheptyloxy which are optionally partially or fully halogenated and optionally substituted with one to three $C_{1-3}$ alkyl groups optionally partially or fully halogenated, wherein one to three ring methylene groups are replaced independently by O, $S(O)_m$, CHOH, >C═O, >C═S or NH;

$R_{20}C(O)N(R_{21})$—, $R_{22}O$— or $R_{23}R_{24}NC(O)$—; $R_{26}(CH_2)_mC(O)N(R_{21})$— or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain optionally partially or fully halogenated, wherein one or more methylene groups are optionally replaced by O, NH, S(O), $S(O)_2$ or S and wherein said alkynyl group is optionally independently substituted with 0-2 oxo groups, pyrroldinyl, pyrrolyl, one or more $C_{1-4}$ branched or unbranched alkyl optionally substituted by one or more halogen atoms, nitrile, morpholino, piperidine, piperazine, imidazole, phenyl, pyridine, tetrazole, or $C_{1-4}$ branched or unbranched alkylamino optionally substituted by one or more halogen atoms; or aroyl;

$R_6$ is a:
$C_{1-4}$ branched or unbranched alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently:
nitrile, morpholino, piperidinyl, piperazinyl, imidazolyl, phenyl, pyridinyl, tetrazolyl or alkylamino mono- or di-$C_{1-4}$ branched or unbranched optionally partially or fully halogenated;

each $R_{11}$ and $R_{16}$ is independently:
hydrogen or $C_{1-4}$ branched or unbranched alkyl optionally partially or fully halogenated;

$R_{18}$ is independently:
hydrogen or a $C_{1-4}$ branched or unbranched alkyl optionally independently substituted with oxo or $R_{25}$;

$R_{20}$ is:
$C_{1-10}$ branched or unbranched alkyl optionally partially or fully halogenated, phenyl or pyridinyl;

$R_{21}$ is:
hydrogen or $C_{1-3}$ branched or unbranched alkyl optionally partially or fully halogenated;

each $R_{22}$, $R_{23}$ and $R_{24}$ is independently:
hydrogen, $C_{1-6}$ branched or unbranched alkyl optionally substituted by carbonylamino-mono- or di-$C_{1-3}$ alkyl or amino-mono or di$C_{1-3}$alkyl or wherein said $C_{1-6}$ alkyl optionally partially or fully halogenated and optionally interrupted by one or more O, N or S, phenyl, pyridine or alkylamino;

or $R_{23}$ and $R_{24}$ taken together optionally form a heterocyclic or heteroaryl ring;

m=0, 1 or 2;

X=O or S; and the pharmaceutically acceptable derivatives thereof.

2. The compound according to claim 1 wherein
Ar is:
pyridinyl, pyrimidinyl, imidazolyl, tetrahydropyranyl, morpholino, thiomorpholino, thiomorpholino sulfoxide, piperidinyl, piperidinonyl or pentamethylene sulfoxide which are optionally substituted with one to three, amino, mono- or di-(phenyl-$C_{1-3}$ alkyl) amino, methyl, ethyl, methoxy, ethoxy, methoxymethyl or ethoxymethyl;

tetrahydropyranyl, tetrahydrofuranyl, morpholino, thiomorpholino, thiomorpholino sulfoxide, piperidinyl, piperidinonyl, tetrahydropyrimidonyl, pentamethylene sulfide, pentamethylene sulfoxide or pentamethylene sulfone which are optionally substituted with one to three $C_{1-3}$ alkyl, $C_{1-3}$ alkoxy, hydroxy, mono- or di-$(C_{1-3}$ alkyl)amino-$C_{1-3}$ alkyl, phenylamino-$C_{1-3}$ alkyl or $C_{1-3}$ alkoxy-$C_{1-3}$ alkyl;

each $R_1$ is independently:
$C_{3-5}$ branched or unbranched alkyl optionally partially or fully halogenated, and optionally substituted with one to three $C_{3-6}$ cycloalkyl, hydroxy, phenyl, thienyl, furyl, isoxazolyl or isothiazolyl each optionally substituted with 1 to 5 halogen, $C_{1-3}$ alkyl which is optionally partially or fully halogenated, hydroxy, cyano or $C_{1-3}$ alkoxy optionally partially or fully halogenated;

cyclopropyl, cyclobutyl, cyclopentanyl, cyclohexanyl, bicyclopentanyl or bicyclohexanyl optionally partially or fully halogenated and optionally be substituted with one to three $C_{1-3}$ alkyl groups optionally partially or fully halogenated, cyano, hydroxy$C_{1-3}$ alkyl or phenyl; or an analog of cyclopropyl, cyclobutyl, cyclopentanyl, cyclohexanyl, bicyclopentanyl or bicyclohexanyl wherein one to three ring methylene groups are independently replaced by O, S, CHOH, >C=O, >C=S or NH; or silyl containing three $C_{1-4}$ independently branched or unbranched alkyl groups optionally partially or fully halogenated;

each $R_3$ is independently:

hydrogen, phenyl, pyridinyl, pyrimidinyl, pyrazinyl, pyrrolyl, pyrrolylidinyl, imidazolyl or pyrazolyl, each optionally substituted with one to five phenyl, naphthyl, heterocycle or heteroaryl as hereinabove described in this paragraph, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, cyano, $C_{1-3}$ alkoxy optionally be partially or fully halogenated, phenyloxy, naphthyloxy, heteraryloxy or heteryclicoxy wherein the heteraryl or heterocyclic moiety is as hereinabove described in this paragraph, nitro, amino, mono- or di-($C_{1-3}$)alkylamino, phenylamino, naphthylamino, heterocyclic or heteroaryl amino wherein the heterocyclic or heteroaryl moiety is as hereinabove described in this paragraph, NH$_2$C(O), a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$) alkylamino-S(O)$_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl ($R_{11}$)N or carboxy-mono- or di-($C_{1-5}$)-alkyl-amino;

$C_{1-3}$ alkyl or $C_{1-3}$ alkoxy optionally partially or fully halogenated or optionally substituted with $R_{17}$;

cyclopropyloxy, cyclopentyloxy or cyclohexyloxy which are optionally partially or fully halogenated and optionally substituted with one to three $C_{1-3}$ alkyl groups optionally partially or fully halogenated, wherein one to three ring methylene groups are replaced independently by O, S(O)$_m$, CHOH, >C=O, >C=S or NH;

$C_{1-6}$ branched branched or unbranched alkyl optionally substituted with OR$_{18}$;

amino or $C_1$-$C_5$ branched or unbranched mono- or di-alkylamino optionally substituted with $R_{19}$;

$R_{20}$C(O)N($R_{21}$)—, $R_{22}$O—; $R_{23}R_{24}$NC(O)—; $R_{26}$CH$_2$C(O)N($R_{21}$)— or $R_{26}$C(O)CH$_2$N($R_{21}$)—;

$C_{2-4}$ alkenyl substituted by $R_{23}R_{24}$NC(O)—;

$C_{2-4}$ alkynyl branched or unbranched carbon chain optionally partially or fully halogenated and optionally independently substituted with 0-2 oxo groups, pyrroldinyl, pyrrolyl or one or more $C_{1-4}$ branched or unbranched alkyl optionally substituted by one or more halogen atoms;

X is O; and $R_{23}$ and $R_{24}$ taken together optionally form imidazole, piperidine, morpholino, piperazine or a pyridinyl ring.

3. The compound according to claim 2 wherein:

Ar is naphthyl;

Q is:

pyridinyl or imidazolyl which are optionally substituted with one to three halogen, $C_{1-3}$ alkyl, $C_{1-3}$ alkoxy, hydroxy, amino, mono- or di-($C_{1-3}$ alkyl) amino or mono- or di-(phenyl-$C_{1-3}$ alkyl)amino;

each $R_1$ is independently:

$C_{3-5}$ branched or unbranched alkyl, optionally partially or fully halogenated, and optionally substituted with phenyl substituted with 0 to 5 halogen, $C_{1-3}$ alkyl optionally partially or fully halogenated, hydroxy, cyano or $C_{1-3}$alkoxy optionally partially or fully halogenated;

cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, CYANO, hydroxy$C_{1-3}$alkyl or phenyl; or an analog of cyclopropyl, cyclobutyl, cyclopentanyl, cyclohexanyl, bicyclopentanyl or bicyclohexanyl wherein one ring methylene group is replaced by O; and silyl containing three $C_{1-2}$ independently branched or unbranched alkyl groups optionally partially or fully halogenated;

each $R_3$ is independently:

hydrogen, phenyl, pyridinyl, pyrimidinyl, pyrrolylidinyl, 2,5-pyrrolidin-dione, imidazolyl, pyrazolyl, each optionally substituted with one to five $C_{1-3}$ alkyl optionally partially or fully halogenated, halogen, oxo, hydroxy, cyano or $C_{1-3}$ alkoxy optionally partially or fully halogenated;

$C_{1-3}$ alkyl or $C_{1-3}$ alkoxy optionally partially or fully halogenated or optionally substituted with $R_{17}$;

Cyclopropyloxy, cyclopentyloxy or cyclohexyloxy which are optionally partially or fully halogenated and optionally substituted with one to three $C_{1-3}$ alkyl groups optionally partially or fully halogenated, wherein one to three ring methylene groups are replaced independently by O, S(O)$_m$, CHOH, >C=O, >C=S or NH;

$C_{1-3}$ branched or unbranched alkyl optionally substituted with OR$_{18}$;

amino or $C_1$-$C_3$ branched or unbranched mono- or di-alkylamino optionally substituted with $R_{19}$;

$R_{20}$C(O)N($R_{21}$)—, $R_{22}$O—; $R_{23}R_{24}$NC(O)—; $R_{26}$CH$_2$C(O)N($R_{21}$)— or $R_{26}$C(O)CH$_2$N($R_{21}$)—;

$C_{2-4}$ alkenyl substituted by $R_{23}R_{24}$NC(O)—; or $C_{2-4}$ alkynyl substituted with pyrroldinyl or pyrrolyl; and $R_{23}$ and $R_{24}$ taken together optionally form morpholino.

4. The compound according to claim 3 wherein:

Ar is 1-naphthyl;

L is a: O—CH$_2$—, O—CH$_2$CH$_2$, O—CH$_2$CH$_2$CH$_2$, O—CH$_2$CH$_2$(CH$_3$), O—CH$_2$(CH$_3$)CH$_2$, NHCH$_2$, NHCH$_2$CH$_2$, NHCH$_2$CH$_2$CH$_2$, S(O)$_m$CH$_2$, S(O)$_m$CH$_2$CH$_2$, S(O)$_m$CH$_2$CH$_2$CH$_2$, CH$_2$CH$_2$, CH$_2$CH$_2$CH$_2$, O—CH$_2$C(O), HC≡C—CH$_2$ or HC≡C—CH$_2$O;

Q is:
  pyridinyl optionally substituted with one to three halogen, $C_{1-3}$ alkyl, $C_{1-3}$ alkoxy, hydroxy, amino, mono- or di-($C_{1-3}$ alkyl)amino or mono- or di-(phenyl-$C_{1-3}$ alkyl)amino;

each $R_1$ is independently:
  $C_{3-5}$ branched or unbranched alkyl optionally partially or fully halogenated, and optionally substituted with phenyl;
  cyclopropyl, cyclopentanyl, cyclohexanyl or bicyclopentanyl optionally substituted with one to three methyl groups optionally partially or fully halogenated, CYANO, hydroxymethyl or phenyl;
  cyclopentyloxy or cyclohexyloxy which are optionally partially or fully halogenated;
  2-tetrahydrofuranyl substituted by methyl; or
  trimethylsilyl;

each $R_3$ is independently:
  hydrogen, phenyl, pyridinyl, pyrimidinyl, pyrrolylidinyl, 2,5-pyrrolidin-dione, imidazolyl or pyrazolyl, each optionally substituted with $C_{1-2}$ alkyl optionally partially or fully halogenated;
  $C_{1-3}$ alkyl or $C_{1-3}$ alkoxy each optionally be partially or fully halogenated or optionally substituted with diethylamino;
  $C_{1-3}$ branched or unbranched alkyl optionally substituted with $OR_{18}$;
  amino or $C_1$-$C_3$ branched or unbranched mono- or di-alkylamino optionally substituted with $R_{19}$;
  $CH_3C(O)NH$—, $R_{22}O$—; $R_{23}R_{24}NC(O)$—; $R_{26}CH_2C(O)N(R_{21})$— or $R_{26}C(O)CH_2N(R_{21})$—;
  $C_{2-4}$ alkenyl substituted by $R_{23}R_{24}NC(O)$—; or
  $C_{2-4}$ alkynyl substituted with pyrroldinyl or pyrrolyl;
  $R_{23}$ and $R_{24}$ are H or $R_{23}$ and $R_{24}$ taken together optionally form morpholino; and
  $R_{26}$ is morpholino.

5. The compound according to claim 3 wherein
Ar is 1-naphthyl;
Q is:
  pyridinyl optionally substituted with one to three halogen, $C_{1-3}$ alkyl, $C_{1-3}$ alkoxy, hydroxy, amino, mono- or di-($C_{1-3}$ alkyl)amino or mono- or di-(phenyl-$C_{1-3}$ alkyl)amino;
L is:
  O, NH, $CH_2$ or S(O)m.

6. The compound according to claim 3 wherein
Ar is 1-naphthyl;
Q is:
  pyridinyl optionally substituted with one to three halogen, $C_{1-3}$ alkyl, $C_{1-3}$ alkoxy, hydroxy, amino, mono- or di-($C_{1-3}$ alkyl)amino or mono- or di-(phenyl-$C_{1-3}$ alkyl)amino;
L is:
  $C(O)CH_2$—, >C(O), O, or $CH_2$;
each $R_1$ is independently:
  $C_{3-5}$ branched or unbranched alkyl optionally partially or fully halogenated, and
each $R_3$ is independently:
  hydrogen, $C_{1-3}$ alkyl or $C_{1-3}$ alkoxy each optionally be partially or fully halogenated or optionally substituted with diethylamino;
  $CH_3C(O)NH$—, $R_{22}O$—; $R_{23}R_{24}NC(O)$—; $R_{26}C(O)N(R_{21})$— or $R_{26}C(O)CH_2N(R_{21})$—;
  $R_{23}$ and $R_{24}$ are H or $R_{23}$ and $R_{24}$ taken together optionally form morpholino; and
  $R_{26}$ is alkylamino mono- or di-$C_{0-4}$ branched or unbranched.

7. The compound according to claims 5 or 6 wherein L is O.

8. A compound selected from:
  1-[4-(2-Amino-pyridin-4-yloxy)-naphthalen-1-yl]-3-(5-tert-butyl-2-methoxy-pyridin-3-yl)-urea;
  1-(5-tert-Butyl-2-methoxy-pyridin-3-yl)-3-[4-(2-methylamino-pyridin-4-yloxy)-naphthalen-1-yl]-urea;
  1-(5-tert-Butyl-2-methoxy-pyridin-3-yl)-3-{4-[2-(1-phenyl-ethylamino)-pyridin-4-yloxy]-naphthalen-1-yl}-urea;
and the pharmaceutically acceptable salts thereof.

9. A pharmaceutical composition comprising a pharmaceutically effective amount of a compound according to claims 1 or 8.

10. A method of treating a disease selected from rheumatoid arthritis, osteoarthritis, Crohn's disease, ulcerative colitis, Guillain-Barre syndrome, psoriasis, systemic lupus erythematosus, toxic shock syndrome, osteoporosis, acute and chronic pain, contact dermatitis and atherosclerosis comprising administering to a patient in need of such treatment a therapeutically effective amount of a compound according to claim 1 or 8.

11. A method of treating a disease selected from thermal injury, acute glomerulonephritis, dermatoses with acute inflammatory components, acute purulent meningitis, hemodialysis, and leukopherisis, comprising administering to a patient in need of such treatment a therapeutically effective amount of a compound according to claim 1 or 8.

12. A method of making a compound of the formula (I):

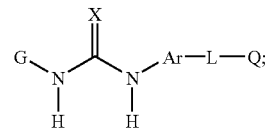

wherein X is O and G, Ar, L and Q are as defined in claim 1,
said method comprising:
a) reacting an arylamine with phenyl chloroformate in a suitable solvent with a suitable base at 0-85° C. for 2-24 hours:

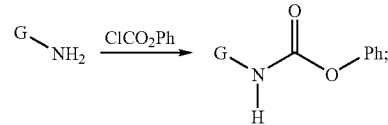

b) reacting the product of step a) with an arylamine shown below in a non-protic anhydrous at 0-110° C. for 2-24 hours, to produce a compound of the formula (I):
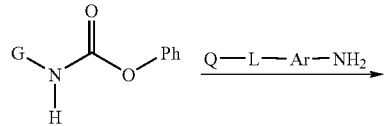
-continued
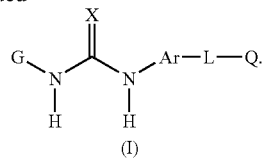
(I)
* * * * *